US011053513B2

(12) United States Patent
Pandey et al.

(10) Patent No.: US 11,053,513 B2
(45) Date of Patent: Jul. 6, 2021

(54) ENHANCED OIL PRODUCTION AND STRESS TOLERANCE IN PLANTS

(71) Applicant: Donald Danforth Plant Science Center, St. Louis, MO (US)

(72) Inventors: Sona Pandey, St. Louis, MO (US); Swarup Roy Choudhry, St. Louis, MO (US)

(73) Assignee: Donald Danforth Plant Science Center, St Louis, MO (US)

( * ) Notice: Subject to any disclaimer, the term of this patent is extended or adjusted under 35 U.S.C. 154(b) by 890 days.

(21) Appl. No.: 14/905,394

(22) PCT Filed: Jul. 15, 2014

(86) PCT No.: PCT/US2014/046757
§ 371 (c)(1),
(2) Date: Jan. 15, 2016

(87) PCT Pub. No.: WO2015/009760
PCT Pub. Date: Jan. 22, 2015

(65) Prior Publication Data
US 2016/0152997 A1    Jun. 2, 2016

Related U.S. Application Data

(60) Provisional application No. 61/846,350, filed on Jul. 15, 2013.

(51) Int. Cl.
*C12N 15/82* (2006.01)

(52) U.S. Cl.
CPC ..... *C12N 15/8274* (2013.01); *C12N 15/8247* (2013.01); *C12N 15/8261* (2013.01); *C12N 15/8271* (2013.01); *C12N 15/8273* (2013.01)

(58) Field of Classification Search
None
See application file for complete search history.

(56) References Cited

U.S. PATENT DOCUMENTS

| | | | |
|---|---|---|---|
| 5,268,463 | A | 12/1993 | Jefferson |
| 5,399,680 | A | 3/1995 | Zhu |
| 5,459,252 | A | 10/1995 | Conkling |
| 5,463,175 | A | 10/1995 | Barry |
| 5,466,785 | A | 11/1995 | De Framond |
| 5,514,578 | A | 5/1996 | Hogness |
| 5,523,311 | A | 6/1996 | Schurter |
| 5,569,597 | A | 10/1996 | Grimsley |
| 5,604,121 | A | 2/1997 | Hilder |
| 5,608,142 | A | 3/1997 | Barton |
| 5,608,144 | A | 3/1997 | Baden |
| 5,608,149 | A | 3/1997 | Barry |
| 5,614,395 | A | 3/1997 | Ryals |
| 5,837,876 | A | 11/1998 | Conkling |
| 5,880,333 | A | 3/1999 | Goff |
| 6,245,531 | B1 | 6/2001 | Hogness |
| 6,379,945 | B1 | 4/2002 | Jepson |
| 6,504,082 | B1 | 1/2003 | Albertsen |
| 6,610,828 | B1 | 8/2003 | Jepson |
| 6,723,531 | B2 | 4/2004 | Evans |
| 6,989,265 | B2 | 1/2006 | Blattner |
| 7,091,038 | B2 | 8/2006 | Palli |
| 7,151,168 | B2 | 12/2006 | Albertsen |
| 7,183,061 | B2 | 2/2007 | Jepson |
| 7,205,455 | B2 | 4/2007 | Albertsen |
| 7,238,859 | B2 | 7/2007 | Albertsen |
| 7,297,781 | B2 | 11/2007 | Hill |
| 7,303,906 | B2 | 12/2007 | Blattner |
| 7,312,322 | B1 | 12/2007 | Hill |
| 7,456,315 | B2 | 11/2008 | Hormann |
| 7,511,190 | B2 * | 3/2009 | Creelman ............ C07K 14/415 800/282 |
| 7,531,326 | B2 | 5/2009 | Kapitskaya |
| 7,563,879 | B2 | 7/2009 | Palli |
| 7,563,928 | B2 | 7/2009 | Hormann |
| 7,601,508 | B2 | 10/2009 | Palli |
| 7,714,190 | B2 * | 5/2010 | da Costa e Silva ....................... C07K 14/415 435/419 |
| 7,776,587 | B2 | 8/2010 | Palli |

(Continued)

FOREIGN PATENT DOCUMENTS

| | | |
|---|---|---|
| CN | 102586264 A * | 7/2012 |
| CN | 102586264 A | 7/2012 |

(Continued)

OTHER PUBLICATIONS

Li et al., New Phytologist, 194:690-703, 2012.*
Smith et al. (Nature Biotechnology, 15:1222-1223, 1997).*
Bork et al. (TIG, 12:425-427, 1996).*
Doerks et al., (TIG, 14:248-250, 1998).*
Fan et al. (Theor. Appl. Genet. 112:1164-1174; Published 2006).*
Li et al. (New Phytologist; 194:690-703; Published 2012).*
Yadav et al. (Plant Signaling and Behavior, 7: 733-740; Published Jul. 1, 2012).*
Wells, Biochemistry 29:8509-8517, 1990, see pp. 8511-8512, tables 1-2.*
Ngo et al., (The Protein Folding Problem and Tertiary Structure Prediction, K. Merz., and S. Le Grand (eds.) pp. 492-495, 1994).*
Guo et al. (PNAS, 101: 9205-9210, 2004).*
Keskin et al. (Protein Science, 13:1043-1055, 2004).*
Thornton et al. (Nature structural Biology, structural genomics supplement, Nov. 2000).*
Nishimura et al. (Plant Cell Physiol., 41 (5):583-590, 2000).*
Yang et al. (PNAS, 98:11438-11443, 2001).*
McConnell et al. (Nature, 411:709-713, 2001).*
Wilkinson et al. (Plant, Cell and Environment, 33:510-525, 2010).*

(Continued)

*Primary Examiner* — Vinod Kumar
(74) *Attorney, Agent, or Firm* — Erica A. Fishel; Charles E. Cohen

(57) ABSTRACT

Provided are plants that express, or overexpress, type III Gγ protein AGG3. Such plants exhibit faster vegetative and reproductive growth, accompanied by an increase in photosynthetic efficiency. Constitutive or seed-specific expression of AGG3 in *Camelina* increases seed size, seed mass, and seed number per plant by 15-40%, effectively resulting in significantly higher oil yield per plant. AGG3-expressing *Camelina* plants also exhibit improved stress tolerance. Use of AGG3 is therefore an effective biotechnological tool to dramatically increase stress tolerance and plant yield, including oil, in agricultural and horticultural crops.

11 Claims, 5 Drawing Sheets

Specification includes a Sequence Listing.

(56) References Cited

U.S. PATENT DOCUMENTS

| | | | |
|---|---|---|---|
| 7,807,417 | B2 | 10/2010 | Palli |
| 7,829,676 | B2 | 11/2010 | Zhang |
| 7,919,269 | B2 | 5/2011 | Zhang |
| 7,935,510 | B2 | 5/2011 | Palli |
| 8,039,243 | B2 | 10/2011 | Blattner |
| 8,043,842 | B2 | 10/2011 | Blattner |
| 8,119,365 | B2 | 2/2012 | Blattner |
| 8,178,339 | B2 | 5/2012 | Campbell |
| 2009/0031451 | A1 | 1/2009 | Da Costa E Silva |
| 2012/0219994 | A1 | 8/2012 | Blattner |

FOREIGN PATENT DOCUMENTS

| | | | |
|---|---|---|---|
| EP | 1483367 B1 | 5/2010 | |
| WO | 2011/120549 A1 | 10/2011 | |
| WO | WO-2011120549 A1 * | 10/2011 | ........... C07K 14/415 |

OTHER PUBLICATIONS

PCT International Search Report in S/N PCT/US14/46757, dated Nov. 21, 2014, 1 pg.
PCT Written Opinion in S/N PCT/US14/46757, dated Nov. 21, 2014, 6 pgs.
Li, et al., "The plant-specific G protein y subunit AGG3 influences organ size and shape in *Arabidopsis thaliana*", New Phytologist 194, 2012, 690-703.
Yadav, et al., "Rice heterotrimeric G-protein gamma subunits (RGG1 and RGG2) are differentially regulated under abiotic stress", Plant Signaling & Behavior, 2012, 7:733-740.
Clauss et al.(2011) Overexpression of sinapine esterase BnSCE3 in oilseed rape seeds triggers global changes in seed metabolism. Plant Physiology, 155 (3):1127-1145.
Shen et al. (2006) The homeobox gene GLABRA2 affects seed oil content in *Arabidopsis*. Plant Molecular Biology, 60 (3): 377-387.

* cited by examiner

SEQUENCE LISTING

<160> NUMBER OF SEQ ID NOS: 9

<210> SEQ ID NO 1
<211> LENGTH: 756
<212> TYPE: DNA
<213> ORGANISM: Arabidopsis thaliana

<400> SEQUENCE: 1
atgtctgctc cttctggcgg tggcgaagga ggaggaaaag aatcagctgc tggtggagtg      60
agttcatcgt ctcttgctcc gtcgtctcta ccaccgcctc gtcctaagtc tccaccagag     120
tatccagatt tgtacgggaa acgcagagag gcggcgagag ttcagatgct cgagagagag     180
attggttttc tcgagggcga aattaaattc atcgaaggcg tacaaccggc atctagatgc     240
atcaaagaag tctctgattt tgttgttgca aattctgacc cattgatccc tgcacaacga     300
aaaagtcgaa gatccttccg gttctggaag tggctctgtg gcccatgttt gagcctggtg     360
agtttctgct gttgctgcca atccaaatgt tcgtgccatc tgaggaaacc caagtgctgc     420
aactgtacat cttgcagctg tatagggtcc aaatgctgtg acgggtcatg ctgctcaaac     480
atttgttgtt gcccgagact aagctgcccg agctgttcat gcttccgagg ttgctggtgt     540
tcttgtccgg acatgtcttg ctgcattccc agctgtttcc gcagttgcag ttgcactcga     600
ccgtcgtgtc tgaataaaaa gaagagctca tgctgcagct gcaactgcaa gatcagatgg     660
tcatcttgtt ttagttgtcc caaggtacga ctttgttctt gttgttttg caattgtaaa      720 aatctatgtt ctaatccttg ttgtttagct ttctaa                              756

<210> SEQ ID NO 2
<211> LENGTH: 2723
<212> TYPE: DNA
<213> ORGANISM: Arabidopsis thaliana

<400> SEQUENCE: 2

```
actactacac actcatctct ctctctttct cttttttcttt cttctttgca ttgtttttct        60
cactcactcg ccgcttcctc ttctcttctt ctggttcact tctctcctaa gtaataacac       120
cactgcatgt ttctctcttg agacactcca aaccatttct ctccgaaaat gtctgctcct       180
tctggcggtg gcgaaggagg aggaaaagaa tcagctgctg gtggagtgag ttcatcgtct       240
cttgctccgt cgtctctacc accgcctcgt cctaagtctc caccagagta tccagatttg       300
tacgggaaac gcagagaggc ggcgagagtt cagatgctcg agagagagat tggttttctc       360
gaggcaagtc tctctctctc aatactttta ttttattact actactacta ctattttaaa       420
aacagtcctt ttcattctta ttttattcat aaaatctgtg ccattttga ttactctgag        480 gaagtgtccc aatattttga atttcatcac tcctttgttt ttattattat tactctctct       540
ttttcaaaaa aaattggtac tagtattagt ttctgattag taaattaatt aatgctaatt       600
aacctctctt gtataactaa ataatccagt tgtagtacta tttgattttt ggttgttgtg       660
agaaaagagt gttaaaactt ggtccctact atatccaggt tggtttggac tctggaccgt       720
tgtgttatgt tttgacagca attatagaaa cccaagacat ttaatttata tttgttctct       780
ttgatgctcc caaaaagaat tattaatttc tgtcatcaga cacatttctc tatttctata       840
tctaattaaa ttcaaactag tactatgata tgccaacaag ggctttaacc acttaaacta       900
atgcatgttt tcttaattga aaattaattt gaatcatttc tcttagtaat ttttttgtta       960
gttgagggag tttcaacgga tctattcttt aaaaactaaa ttaattgggt tcctatgctt      1020
ttcgttaatc aggatttttt ttgggttata gaatattgtt agtagttaca ttctgttta        1080 aaattaagga tacataaaaa aaaaaagta aaaaaaatgt taaggtaaa aaaaaaaat          1140 gtgatcatgt tgtagtgtga agtgaccgat gagacgccca tttactcagt tgtttgcatc      1200
actgaggcct aatgtgttcg tgcatgtgta ctatgaaagt gagtgcttag tcaaagagag      1260
tattaaaggg aaaaatacat aaagataaag aagaaaagca ttagaagcaa agtagggaaa      1320
gatctaaaaa atatattgaa tttggttagc ttccattgct gattttgttt tgttttgctt      1380
tgccatatca atcaatttt gtgaaagctt ttgtctttat tgctatctgc gtttgaaagg       1440
accaattctt ggtcaccttt ttcctcatgt tgctttctca tttccccctc tatgattact      1500
ttttctatag tgcatataat tggttgtaat taaattattt tttacactgt atatgtttag      1560
tttaatatgc aattcttgtt ttgtcccatt agtgtctact taatttagat cttctcttt       1620 tttaaccaag caaatacaat ttggttgatt aatgaaatga tgtttcttaa ccaatatttc      1680
gaatgtcgtt atgatcaggg cgaaattaaa ttcatcgaag gcgtacaacc ggcatctaga      1740
tgcatcaaag agtgagtgtt ttaaaaacat tctatcagtt tttatcagtt tggtttattg      1800 ataaagaaa tattttgttg tggcagagtc tctgattttg ttgttgcaaa ttctgaccca       1860
ttgatccctg cgtaagcgta tttctagttc actcaatgac ttcacactt tctcgtactt        1920 tgcccgctct tacaattccg ttgtgctgtt tttgtcttct catataaata gacaacgaaa      1980
aagtcgaaga tccttccggt tctggaagtg gctctggtaa gcatttaaat tggaacatta      2040
tattttgaaa atatttaatt ttcgcaattt tatataaaat ttgcataaga cctcaactag      2100
taagaaatgt ttttagccaa tgcttttaat cttagatttt gctagaatta ctgatatgtg      2160
tagctatctg aataaagtga tactaattaa ttaactcaat gcagtggccc atgtttgagc      2220
ctggtgagtt tctgctgttg ctgccaatcc aaatgttcgt gccatctgag gaaacccaag      2280
tgctgcaact gtacatcttg cagctgtata gggtccaaat gctgtgacgg tcatgctgc       2340
```

-continued

```
tcaaacattt gttgttgccc gagactaagc tgcccgagct gttcatgctt ccgaggttgc    2400
tggtgttctt gtccggacat gtcttgctgc attcccagct gtttccgcag ttgcagttgc    2460
actcgaccgt cgtgtctgaa taaaagaag agctcatgct gcagctgcaa ctgcaagatc     2520
agatggtcat cttgttttag ttgtcccaag gtacgacttt gttcttgttg tttttgcaat    2580
tgtaaaaatc tatgttctaa tccttgttgt ttagctttct aattaaactt tattattatt    2640
ataatcatta tagctgtttc ctctattttt tgttcaaatt ttttcttaat ctcttaaagg    2700
aagcaacact ttcttgattt tgt                                             2723
```

<210> SEQ ID NO 3
<211> LENGTH: 251
<212> TYPE: PRT
<213> ORGANISM: Arabidopsis thaliana

<400> SEQUENCE: 3

```
Met Ser Ala Pro Ser Gly Gly Glu Gly Gly Lys Glu Ser Ala
1               5                   10                  15

Ala Gly Gly Val Ser Ser Ser Leu Ala Pro Ser Ser Leu Pro Pro
                20                  25                  30

Pro Arg Pro Lys Ser Pro Glu Tyr Pro Asp Leu Tyr Gly Lys Arg
        35                  40                      45

Arg Glu Ala Ala Arg Val Gln Met Leu Glu Arg Ile Gly Phe Leu
    50                  55                  60

Glu Gly Glu Ile Lys Phe Ile Glu Gly Val Gln Pro Ala Ser Arg Cys
65                  70                  75                  80

Ile Lys Glu Val Ser Asp Phe Val Val Ala Asn Ser Asp Pro Leu Ile
                85                  90                  95

Pro Ala Gln Arg Lys Ser Arg Arg Ser Phe Arg Phe Trp Lys Trp Leu
            100                 105                 110

Cys Gly Pro Cys Leu Ser Leu Val Ser Phe Cys Cys Cys Gln Ser
        115                 120                 125

Lys Cys Ser Cys His Leu Arg Lys Pro Lys Cys Cys Asn Cys Thr Ser
    130                 135                 140

Cys Ser Cys Ile Gly Ser Lys Cys Cys Asp Gly Ser Cys Ser Asn
145                 150                 155                 160

Ile Cys Cys Cys Pro Arg Leu Ser Cys Pro Ser Cys Ser Cys Phe Arg
                165                 170                 175

Gly Cys Trp Cys Ser Cys Pro Asp Met Ser Cys Cys Ile Pro Ser Cys
            180                 185                 190

Phe Arg Ser Cys Ser Cys Thr Arg Pro Ser Cys Leu Asn Lys Lys
        195                 200                 205

Ser Ser Cys Cys Ser Cys Asn Cys Lys Ile Arg Trp Ser Ser Cys Phe
    210                 215                 220

Ser Cys Pro Lys Val Arg Leu Cys Ser Cys Cys Phe Cys Asn Cys Lys
225                 230                 235                 240

Asn Leu Cys Ser Asn Pro Cys Cys Leu Ala Phe
                245                 250
```

<210> SEQ ID NO 4
<211> LENGTH: 25
<212> TYPE: DNA
<213> ORGANISM: Artificial Sequence
<220> FEATURE:
<223> OTHER INFORMATION: PCR Primer

<400> SEQUENCE: 4

```
atgtctgctc cttctggcgg tggcg                                              25

<210> SEQ ID NO 5
<211> LENGTH: 26
<212> TYPE: DNA
<213> ORGANISM: Artificial Sequence
<220> FEATURE:
<223> OTHER INFORMATION: PCR Primer

<400> SEQUENCE: 5
ttagaaagct aaacaacaag gattag                                             26

<210> SEQ ID NO 6
<211> LENGTH: 31
<212> TYPE: DNA
<213> ORGANISM: Artificial Sequence
<220> FEATURE:
<223> OTHER INFORMATION: PCR Primer

<400> SEQUENCE: 6
atgcgaattc atgtctgctc cttctggcgg t                                       31

<210> SEQ ID NO 7
<211> LENGTH: 28
<212> TYPE: DNA
<213> ORGANISM: Artificial Sequence
<220> FEATURE:
<223> OTHER INFORMATION: PCR Primer

<400> SEQUENCE: 7
atgctcgcga ttagaaagct aaacaaca                                           28

<210> SEQ ID NO 8
<211> LENGTH: 20
<212> TYPE: DNA
<213> ORGANISM: Artificial Sequence
<220> FEATURE:
<223> OTHER INFORMATION: RT PCR Primer

<400> SEQUENCE: 8
cttgctccgt cgtctctacc                                                    20

<210> SEQ ID NO 9
<211> LENGTH: 20
<212> TYPE: DNA
<213> ORGANISM: Artificial Sequence
<220> FEATURE:
<223> OTHER INFORMATION: RT PCR Primer

<400> SEQUENCE: 9
gcatctagat gccggttgta                                                    20
```

ENHANCED OIL PRODUCTION AND STRESS TOLERANCE IN PLANTS

CROSS REFERENCE TO RELATED APPLICATIONS

This application is the United States National Phase entry of International Application No. PCT/US2014/046757, filed Jul. 15, 2014, which claims the benefit of priority of U.S. Provisional Application Ser. No. 61/846,350, filed Jul. 15, 2013, the contents of which are herein incorporated by reference in their entireties.

STATEMENT REGARDING FEDERALLY SPONSORED RESEARCH OR DEVELOPMENT

The development of this invention was partially funded by the government under grant number 2010-65116-20454 awarded by the United States Department of Agriculture/Agriculture and Food Research Initiative. The government has certain rights in the invention.

REFERENCE TO SEQUENCE LISTING

The material contained in the text file identified as "DDPSC0048-401-PC_20140708_SequenceListing_ASFILED" (created Jan. 14, 2016; 81.0 Kilobytes) is hereby incorporated by reference in its entirety.

BACKGROUND

Field of the Invention

The present invention relates to the field of plant molecular biology. More particularly, the present invention relates to transgenic plants exhibiting enhanced oil production and stress tolerance, to increase yield and health of plants in general, as well as in periods of stress.

Description of Related Art

Plant Yield and Stress Resistance

Seed and fruit production are multi-billion dollar commercial industries and primary sources of income for numerous states in the United States and for many countries around the world. Plant oils, derived from seeds and fruits, are major commodities for food and feed, and have increasingly become an important source for biofuels and renewable industrial chemicals. Inadequate supply of plant oils is a major challenge to broadening their biofuel and industrial applications. Thus, there remains a significant unmet need to develop plants that exhibit significantly enhanced oil content.

Seed and fruit production are both inherently limited due to biotic and abiotic stresses. Improvement of abiotic stress tolerance in plants would be an agronomic advantage to growers, increasing growth and/or germination, and yield, in the presence of cold, drought, flood, heat, UV stress, ozone increases, acid rain, pollution, salt stress, heavy metals, mineralized soils, and other abiotic stresses. Biotic stresses, such as fungal and viral infection, also cause large crop yield losses worldwide.

Plant yield is a complex trait involving the interaction of many biochemical pathways and interacting factors on a molecular basis. Many agronomic traits can affect yield including, without limitation, grain or seed size, resistance to biotic and abiotic stress, carbon assimilation, seed composition (starch, oil, protein), and characteristics of seed fill.

In a simplified view, the yield of a plant ultimately depends on the energy the plant gains through fixing carbon dioxide into carbohydrates during photosynthesis. The primary sources of photosynthesis are the leaves, and to a lesser extent stem tissue. Other organs of the plant, such as roots, seeds or tubers, do not make a material contribution to the formation of photoassimilates, and instead are dependent for their growth on the supply of carbohydrates received from photosynthetically active organs. This means that there is a flow of photosynthetically gained energy from photosynthetically active tissues to photosynthetically inactive tissues. Translocation occurs from areas of supply (sources) to areas of metabolism or storage (sinks). Alteration of the primary processes of photosynthesis and/or the metabolic pathways that lead to the synthesis of storage substances such as starch, proteins, fats, or oils results in differential distribution of photoassimilates within the plant, a process known as carbon partitioning.

Many factors influence seed size. Substantial variability in seed size may be due to the position of the seeds within the plant or the inflorescence, variations in moisture content, or perturbations of photosynthetic and/or metabolic pathways. Changes in seed size often result from alteration in carbon partitioning. For example, Clauss et al. (2011) discloses that overexpression of sinapine esterase BnSCE3 results in significantly increased weight, size, and water content of transgenic seeds compared to control plants. Strikingly, while the transgenic plants had larger seeds, the oil and protein contents differed only slightly. Instead, carbohydrates such as hemicellulose and cellulose were about 30% higher in transgenic compared with wild-type seeds (Clauss et al. 2011). In another example, Shen et al. (2006) discloses that in a high oil mutant, p777, seeds accumulated 8% more oil than control plants, but showed no differences in seed size, plant growth or development.

These results demonstrate that due to the hierarchal series of controls, regulation, crosstalk, and feedbacks from the genetic to the physiological level, no direct relationship can be established between seed size and oil to protein to carbohydrate ratio, i.e., increased seed size or mass does not necessarily lead to proportionately increased oil production and/or accumulation.

Roles of GTP-Binding Proteins (G-Proteins) in Plants

Heterotrimeric GTP-binding proteins (G-proteins) are important regulators of multiple growth and developmental pathways in all eukaryotes. This protein complex, consisting of Gα, Gβ, and Gγ subunits, switches between active and inactive conformation depending on the guanine nucleotide-bound status of Gα protein. GDP-Gαβγ trimeric complex represents the inactive state of signaling which results in formation of GTP-Gα and freed Gβγ upon a signal-dependent exchange of GDP for GTP on Gα. Both these entities can transduce the signal downstream by interacting with various intracellular effectors. The intrinsic GTPase activity of Gα protein causes hydrolysis of bound GTP, returning it to its GDP-bound state, which re-associates with the Gβγ proteins to return to the GDP-Gαβγ conformation (Cabrera-Vera et al., 2003; Offermanns, 2003). In plants, the involvement of G-proteins has been established in regulation of a multitude of fundamental growth and development pathways such as phytohormone signaling and cross-talk, cell division, ion channel regulation, defense responses, and reproductive trait plasticity (Urano et al., 2013).

Though evolutionarily conserved, plants contain fewer numbers of heterotrimeric G-proteins compared to their mammalian counterparts. While 23 Gα, 5 Gβ, and 12 Gγ subunits are present in humans, the model plant *Arabidopsis*

*thaliana* has only one Gα, one Gβ, and three Gγ-proteins (Temple and Jones, 2007). In this plant, the specificity of heterotrimer formation is thus solely provided by the Gγ proteins. The plant Gγ proteins are fairly diverse, and can be classified into three different subtypes based on their structural features: type I, II, and III (Roy Choudhury et al., 2011). The type I and II families exhibit most of the conserved features of canonical mammalian Gγ proteins. The type III Gγ proteins, represented by AGG3 in *Arabidopsis*, and GmGγ8, GmGγ9, and GmGγ10 in soybean, are recently discovered novel, plant-specific proteins (Chakravorty et al., 2011; Li et al., 2012; Roy Choudhury et al., 2011). These proteins are almost twice as large as other known Gγ proteins. The N-terminal half of these proteins exhibits a high degree of similarity with canonical Gγ proteins, whereas the C-terminal half (70-140 amino acids) is plant-specific and contains an extremely high number of cysteine (Cys) residues.

Functional analysis of *Arabidopsis* AGG3 shows its involvement in G-protein mediated abscisic acid (ABA) signaling during stomatal aperture control, seed germination, and post-germination growth (Chakravorty et al., 2011). Similarly, in soybean, the type III Gγ proteins are involved during ABA-dependent inhibition of nodule formation and during lateral root formation in transgenic soybean hairy roots (Roy Choudhury and Pandey, 2013).

In addition, a novel role for the group III Gγ proteins emerged in the control of organ size and architecture based on the phenotypes of multiple rice mutants. Two previously identified quantitative trait loci (QTLs) for seed size and number, DEP1 (dense and erect panicle 1) and GS3 (grain size 3), encode for possible homologs of type III Gγ proteins (Fan et al., 2009; Huang et al., 2009; Takano-Kai et al., 2009; Mao et al., 2010). Targeted knockout and overexpression of the AGG3 gene in *Arabidopsis* supports its role in regulation of organ size. The AGG3 knockout mutants have relatively smaller and fewer seeds per silique, whereas *Arabidopsis* plants overexpressing this gene have slightly larger and more seeds per plant (Chakravorty et al., 2011; Li et al., 2012).

Although Li et al. (2012) teaches a relationship between AGG3 and seed size, this reference neither teaches nor suggests any effects of AGG3 on oil composition and content of the seeds. Furthermore, no relationship between type III Gγ proteins, such as AGG3, and oil production or redox stress tolerance in plants has been reported in the literature.

With the world population expected to reach 9 billion people by 2050, ever-rising demand for food, feed, fiber, and fuel presents significant challenges to agriculture. In order to satisfy this demand, crop yield improvement has been one of the major goals of plant biology research. Based on extensive studies in model plant systems over the years, multiple genes regulating a variety of different pathways have been suggested to improve yield and/or provide stress tolerance. However, with the exception of a few cases, the translation of such knowledge to important food and fuel crops is only beginning to be evaluated (Parry and Hawkesford, 2010; Parry and Hawkesford, 2012; Peterhansel and Offermann, 2012; Rojas et al., 2010; Ruan et al., 2012).

Thus, there exists a need in the art for new plants with further improved traits. Traditional breeding (crossing specific alleles of one genotype into another) has been used for centuries to increase biotic stress tolerance, abiotic stress tolerance, and yield. However, traditional breeding is inherently limited to the limited number of alleles present in the parental plants, which limits the amount of genetic variability that can be added in this manner.

The present invention addresses this problem. The inventor has surprisingly discovered that expression (or overexpression) of *Arabidopsis* type III Gγ protein AGG3 in *Camelina* enhances resistance to redox stresses, and enhances oil content in seeds of this oil crop plant. Neither of these effects is either disclosed or suggested by previous studies of the AGG3 type III Gγ protein in plants. While previous studies suggest that AGG3 overexpression in *Arabidopsis* results in slightly larger and more seeds per plant (Chakravorty et al., 2011; Li et al., 2012), and two previously identified quantitative trait loci (QTLs) for seed size and number, DEP1 (dense and erect panicle 1) and GS3 (grain size 3), encode for possible homologs of type III Gγ proteins (Fan et al., 2009; Huang et al., 2009; Takano-Kai et al., 2009; Mao et al., 2010), the work of Clauss et al. (2011) and Shen et al. (2006), discussed above, demonstrates that there is not necessarily a direct relationship between seed size and oil to protein to carbohydrate ratio. Thus, increased seed size or mass does not inevitably result in proportionately increased oil production and/or accumulation, i.e., there is no direct correlation between increased seed size or mass and increased oil accumulation.

Thus, the methods disclosed herein, and transgenic plants produced thereby, provide an improved approach for the large scale production of commercially important oils in plants, with the potential to directly provide a renewable source of hydrocarbons, suitable for use for the production of food and feed additives, fuels, organic solvents, plastics, medicinal substances, and high value industrial raw materials and chemical intermediates. These methods also facilitate production of plants, including crop plants and oil crop plants, with improved resistance to redox stresses in their environment, and therefore improved overall plant health and yield.

SUMMARY

Accordingly, among its many aspects, the present invention provides:

1. A transgenic plant, other than a rice plant or *Arabidopsis*, which exhibits enhanced resistance to a redox stress compared to the resistance to a redox stress exhibited by an otherwise identical control plant grown under the same conditions,
   wherein said transgenic plant comprises within its genome a heterologous nucleotide sequence that encodes a type III Gγ protein, and which is expressed.
2. The transgenic plant of claim 1, wherein said type III Gγ protein is expressed in cells of said plant at a level effective to confer enhanced resistance to said redox stress.
3. The transgenic plant of claim 1 or 2, wherein said type III Gγ protein is expressed under the control of a constitutive or tissue-specific promoter.
4. The transgenic plant of any one of claims 1-3, wherein said redox stress is caused by an abiotic stress that disrupts the normal redox state of plants.
5. The transgenic plant of claim 4, wherein said abiotic stress is selected from the group consisting of cold, heat, drought, flood, ionizing or non-ionizing radiation, acid rain, an air pollutant, a water or soil pollutant, mineralized soil, a pesticide, and a herbicide.

6. The transgenic plant of claim 5, wherein said air pollutant is elevated carbon dioxide, ozone, or sulfur dioxide, and said water or soil pollutant is a salt or heavy metal.

7. The transgenic plant of any one of claims 1-6, wherein said enhanced resistance to said redox stress is in the range from about 10% to about 15% greater than that exhibited by said otherwise identical control plant when both plants are grown under the same conditions.

8. The transgenic plant of any one of claims 1-7, which is a food crop plant or an oil crop plant.

9. The transgenic plant of claim 8, wherein said food crop plant is selected from the group consisting of a cereal crop, a protein crop, a root or tuber, a sugar crop, a fruit crop, a vegetable crop, a nut crop, a forage or turf grass, a forage legume, a drug crop, and a spice or flavoring crop.

10. The transgenic plant of claim 8, wherein said oil crop plant is selected from the group consisting of corn, soybean, canola (rapeseed), wheat, peanut, palm, coconut, safflower, sesame, cottonseed, sunflower, flax, olive, safflower, sugarcane, castor bean, *Camelina*, switchgrass, *Miscanthus*, and *Jatropha*.

11. A transgenic oil crop plant, which produces an enhanced amount of oil compared to the amount of oil produced by an otherwise identical control plant grown under the same conditions,
    wherein said transgenic oil crop plant comprises within its genome a heterologous nucleotide sequence that encodes a type III Gγ protein, and which is expressed.

12. The transgenic oil crop plant of claim 11, wherein said type III Gγ protein is expressed at a level effective to enhance the amount of oil in said plant.

13. The transgenic oil crop plant of claim 11 or 12, wherein said heterologous nucleotide sequence that encodes said type III Gγ protein is expressed under the control of a constitutive promoter or a tissue-specific promoter.

14. The transgenic oil crop plant of any one of claims 11-13, which is selected from the group consisting of corn, soybean, canola (rapeseed), wheat, peanut, palm, coconut, safflower, sesame, cottonseed, sunflower, flax, olive, safflower, sugarcane, castor bean, *Camelina*, switchgrass, *Miscanthus*, and *Jatropha*.

15. The transgenic oil crop plant of any one of claims 11-14, wherein said enhanced amount of oil accumulates in a part of said plant selected from the group consisting of an inflorescence, a flower, a seed, a fruit, a leaf, a stem, a root, a tuberous root, a rhizome, a tuber, a stolon, a corm, a bulb, and an offset, or in a cell of said plant in culture, a tissue of said plant in culture, an organ of said plant in culture, and a callus.

16. The transgenic plant of any one of claims 1-15, wherein said type III Gγ protein is AGG3.

17. The transgenic plant of claim 16, wherein said AGG3 protein comprises the amino acid sequence shown in SEQ ID NO:3.

18. A method of obtaining oil from seeds of an oilseed crop plant, comprising:
    expressing a heterologous nucleotide sequence that encodes a type III Gγ protein in said oilseed crop plant, and
    recovering oil from said seeds of said oilseed crop plant,
    wherein the amount of oil obtained from said oilseed crop plant is greater than that obtained from an otherwise identical control oilseed crop plant grown under the same conditions.

19. The method of claim 18, wherein said heterologous nucleotide sequence is expressed under the control of a constitutive promoter or a seed-specific promoter.

20. The method of claim 18 or 19, wherein said oilseed crop plant is selected from the group consisting of corn, soybean, canola (rapeseed), wheat, peanut, palm, coconut, safflower, cottonseed, sunflower, flax, olive, safflower, castor bean, *Camelina*, and *Jatropha*.

21. The method of any one of claims 18-20, wherein said type III Gγ protein is AGG3.

22. The method of claim 21, wherein said AGG3 protein comprises the amino acid sequence shown in SEQ ID NO:3.

23. A method of obtaining an edible oil, comprising extracting and recovering edible oil produced by a transgenic plant of any one of claims 11-17.

24. The method of claim 23, wherein said edible oil is a cooking oil, a baking oil, a frying oil, a salad oil, or a nutritional supplement.

25. A method of producing a food product containing an edible oil, comprising incorporating edible oil produced by, and extracted and recovered from, a transgenic plant of any one of claims 11-17 into said food product.

26. A method of producing an oil-containing product selected from the group consisting of a cosmetic, a food supplement, a soap, a biofuel, a paint, a medicinal product, an aromatherapy product, a perfume or fragrance, a drying oil, a lubricant, an industrial oil, and a cleaning product, comprising incorporating oil produced by, and extracted and recovered from, a transgenic plant of any one of claims 11-17 into said oil-containing product.

27. A transgenic plant other than rice or *Arabidopsis*, wherein said transgenic plant comprises within its genome a heterologous nucleotide sequence that encodes a type III Gγ protein, and which is expressed.

28. The transgenic plant of claim 27, which exhibits enhanced resistance to a redox stress compared to the resistance to a redox stress exhibited by an otherwise identical control plant grown under the same conditions.

29. The transgenic plant of claim 27, which produces an enhanced amount of oil compared to the amount of oil produced by an otherwise identical control plant grown under the same conditions.

30. A transgenic plant other than rice or *Arabidopsis*,
    which exhibits enhanced resistance to a redox stress compared to the resistance to a redox stress exhibited by an otherwise identical control plant grown under the same conditions, and
    which produces an enhanced amount of oil compared to the amount of oil produced by an otherwise identical control plant grown under the same conditions,
    wherein said transgenic plant comprises within its genome a heterologous nucleotide sequence that encodes a type III Gγ protein, and which is expressed.

31. Progeny of said transgenic plant of any one of claim 1-17 or 27-30.

32. The progeny of claim 31, which is produced sexually.

33. The progeny of claim 31, which is produced asexually.

34. The progeny of claim 33, which are produced asexually from cuttings.

35. A part of said plant or progeny of any one of claim 1-17 or 27-34, respectively.
36. The part of said plant or progeny of claim 35, which is selected from the group consisting of a protoplast, a cell, a tissue, an organ, a cutting, and an explant.
37. The part of said plant or progeny of claim 35, which is selected from the group consisting of an inflorescence, a flower, a sepal, a petal, a pistil, a stigma, a style, an ovary, an ovule, an embryo, a receptacle, a seed, a fruit, a stamen, a filament, an anther, a male or female gametophyte, a pollen grain, a meristem, a terminal bud, an axillary bud, a leaf, a stem, a root, a tuberous root, a rhizome, a tuber, a stolon, a corm, a bulb, an offset, a cell of said plant in culture, a tissue of said plant in culture, an organ of said plant in culture, and a callus.
38. A method of making a plant, other than rice or *Arabidopsis*, that exhibits enhanced resistance to a redox stress compared to the resistance to a redox stress exhibited by an otherwise identical control plant grown under the same conditions, comprising expressing a heterologous nucleotide sequence that encodes a type III Gγ protein within cells of said plant.
39. A method of making an oil crop plant that produces an enhanced amount of oil compared to the amount of oil produced by an otherwise identical control plant grown under the same conditions, comprising expressing a heterologous nucleotide sequence that encodes a type III Gγ protein within cells of said oil crop plant.
40. A method of making a transgenic plant, other than rice or *Arabidopsis*,
    that exhibits enhanced resistance to a redox stress compared to the resistance to a redox stress exhibited by an otherwise identical control plant grown under the same conditions, and
    that produces an enhanced amount of oil compared to the amount of oil produced by an otherwise identical control plant grown under the same conditions,
    comprising expressing a heterologous nucleotide sequence that encodes a type III Gγ protein within cells of said plant.

The present disclosure provides for:
1. A transgenic plant, other than a rice plant or *Arabidopsis*, with enhanced resistance to a redox stress comprising expressing in said transgenic plant a DNA construct comprising a promoter that functions in plants, operably linked to a DNA polynucleotide molecule selected from the group consisting of:
   a. a DNA molecule encoding a polypeptide sequence at least 90% identical to SEQ ID NO:3; and
   b. a DNA molecule comprising the polynucleotide sequence of SEQ ID NO:1 wherein said transgenic plant exhibits enhanced resistance to a redox stress compared to a plant of a same plant species not containing the DNA construct.
2. The transgenic plant of claim 1, wherein said DNA molecule is expressed in cells of said plant at a level effective to confer enhanced resistance to said redox stress.
3. The transgenic plant of claim 2, wherein said DNA molecule is expressed under the control of a heterologous plant promoter.
4. The transgenic plant of claim 1 wherein said redox stress is caused by an abiotic stress that disrupts the normal redox state of plants.
5. The transgenic plant of claim 4, wherein said abiotic stress is selected from the group consisting of cold, heat, drought, flood, ionizing or non-ionizing radiation, acid rain, an air pollutant, a water or soil pollutant, mineralized soil, a pesticide, and a herbicide.
6. The transgenic plant of claim 5, wherein said air pollutant is elevated carbon dioxide, ozone, or sulfur dioxide, and said water or soil pollutant is a salt or heavy metal.
7. The transgenic plant of claim 1, wherein said enhanced resistance to said redox stress is in the range from about 10% to about 15% greater than that exhibited by said otherwise identical control plant when both plants are grown under the same conditions.
8. The transgenic plant of claim 1, wherein said DNA molecule is expressed in cells of said plant to produce an enhanced amount of oil compared to the amount of oil produced by an otherwise identical control plant grown under the same conditions.
9. The transgenic plant of claim 1, wherein said plant is a crop plant.
10. The transgenic plant of claim 9, wherein said crop plant is selected from the group consisting of corn, soybean, rapeseed/canola, wheat, peanut, palm, coconut, safflower, sesame, cottonseed, sunflower, flax, olive, safflower, sugarcane, castor bean, *Camelina*, switchgrass, *Miscanthus*, and *Jatropha*.
11. The transgenic plant of claim 8, wherein said enhanced amount of oil accumulates in a part of said plant selected from the group consisting of an inflorescence, a flower, a seed, a fruit, a leaf, a stem, a root, a tuberous root, a rhizome, a tuber, a stolon, a corm, a bulb, and an offset, or in a cell of said plant in culture, a tissue of said plant in culture, an organ of said plant in culture, and a callus.
12. The transgenic plant of claim 1, wherein said polypeptide is an AGG3 protein.
13. The transgenic plant of claim 12, wherein said AGG3 protein comprises the amino acid sequence shown in SEQ ID NO:3.
14. A method of generating a transgenic plant, other than a rice plant or *Arabidopsis*, with enhanced resistance to a redox stress comprising expressing in said transgenic plant a DNA construct comprising a promoter that functions in plants, operably linked to a DNA polynucleotide molecule selected from the group consisting of:
    a. a DNA molecule encoding a polypeptide sequence at least 90% identical to SEQ ID NO:3; and
    b. a DNA molecule comprising the polynucleotide sequence of SEQ ID NO:1
    wherein said transgenic plant exhibits enhanced resistance to a redox stress compared to a plant of a same plant species not containing the DNA construct.
15. A method of obtaining oil from seeds of an oilseed crop plant, comprising:
    expressing a heterologous nucleotide sequence that encodes a type III Gγ protein in said oilseed crop plant, and
    recovering oil from said seeds of said oilseed crop plant,
    wherein the amount of oil obtained from said oilseed crop plant is greater than that obtained from an otherwise identical control oilseed crop plant grown under the same conditions.

Further scope of the applicability of the present invention will become apparent from the detailed description and drawing(s) provided below. However, it should be understood that the detailed description and specific examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

The above and other aspects, features, and advantages of the present invention will be better understood from the following detailed description taken in conjunction with the accompanying drawing(s), all of which are given by way of illustration only, and are not limitative of the present invention, in which.

DETAILED DESCRIPTION OF THE INVENTION

Figure 1A:
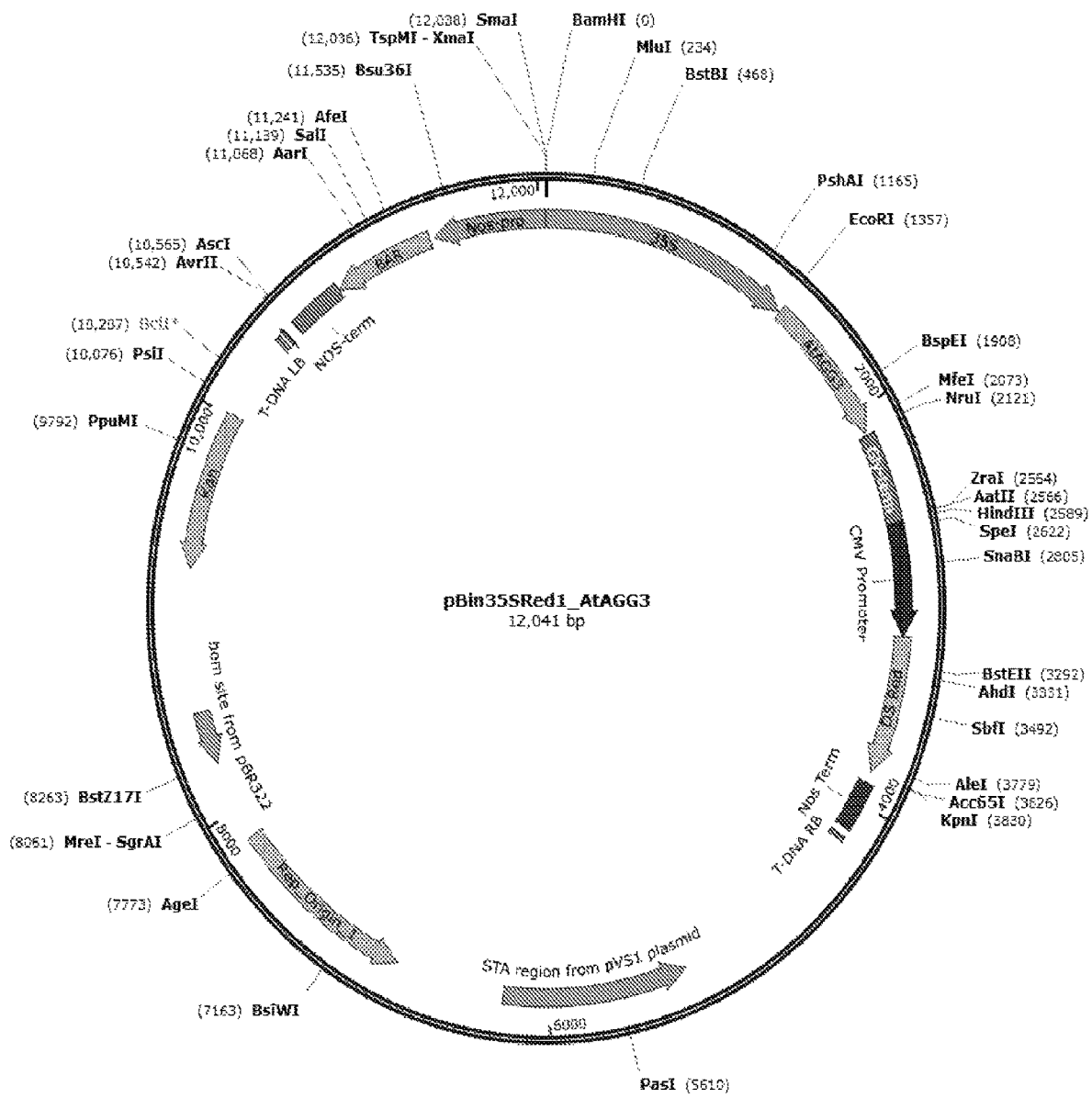
FIG. 1 shows the constructs for overexpression of *Arabidopsis* AGG3 cDNA (SEQ ID NO:1) in *Camelina sativa*. Generation of constructs for constitutive (pBin35SRed1_AtAGG3; A) and seed-specific glycinin promoter (pBinGlyRed1_AtAGG3; B) driven overexpression of AGG3 are shown. The selection markers, Ds-Red and Bar (basta resistance) are driven by the CaMV promoter and Nos promoter, respectively.

The following detailed description of the invention is provided to aid those skilled in the art in practicing the present invention. Even so, the following detailed description should not be construed to unduly limit the present invention, as modifications and variations in the embodiments herein discussed may be made by those of ordinary skill in the art without departing from the spirit or scope of the present inventive discovery.

The following definitions are provided to aid the reader in understanding the various aspects of the present invention. Unless defined otherwise, all technical and scientific terms used herein have the same meaning as commonly understood by those of ordinary skill in the art to which the invention pertains. Provision, or lack of the provision, of a definition for a particular term or phrase is not meant to signify any particular importance, or lack thereof. Rather, and unless otherwise noted, terms are to be understood according to conventional usage by those of ordinary skill in the art. For example, definitions of common terms used in molecular biology and molecular genetics can be found in J. Kendrew, Ed., *The Encyclopedia of Molecular Biology*, Blackwell Science Ltd., Oxford, 1995; Lewin, *Genes IX*, Oxford University Press and Cell Press, New York, 2006; Buchanan, et al., *Biochemistry and Molecular Biology of Plants*, Courier Companies, USA, 2000; Alberts, et al., *Molecular Biology of the Cell* ($5^{th}$ edition), 2008; and Lodish et al., *Molecular Cell Biology* ($7^{th}$ edition), W.H. Freeman Company, New York, 2013. The nomenclature for DNA bases as set forth in 37 CFR § 1.822 is used.

The contents of each of the documents cited herein are herein incorporated by reference in their entirety.

Definitions

If ranges are disclosed, the endpoints of all ranges directed to the same component or property are inclusive and independently combinable (e.g., ranges of "up to about 25 wt. %, or, more specifically, about 5 wt. % to about 20 wt. %," is inclusive of the endpoints and all intermediate values of the ranges of "about 5 wt. % to about 25 wt. %," etc.).

About: The term "about" as used herein is a flexible word with a meaning similar to "approximately" or "nearly". The term "about" indicates that exactitude is not claimed, but rather a contemplated variation. Thus, as used herein, the term "about" means within 1 or 2 standard deviations from the specifically recited value, or ±a range of up to 20%, up to 15%, up to 10%, up to 5%, or up to 4%, 3%, 2%, or 1% compared to the specifically recited value.

The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. and R. H. Schirmer (1979) *Principles of Protein Structure*, Springer-Verlag). According to such analyses, groups of amino acids can be defined where amino acids within a group exchange preferentially with each other, and therefore resemble each other most in their impact on the overall protein structure.

Examples of amino acid groups defined in this manner include: a "charged/polar group," consisting of Glu, Asp, Asn, Gln, Lys, Arg and His; an "aromatic, or cyclic group," consisting of Pro, Phe, Tyr and Trp; and an "aliphatic group" consisting of Gly, Ala, Val, Leu, Ile, Met, Ser, Thr and Cys. Within each group, subgroups can also be identified, for example, the group of charged/polar amino acids can be sub-divided into the sub-groups consisting of the "positively-charged sub-group," consisting of Lys, Arg and His; the negatively-charged sub-group," consisting of Glu and Asp, and the "polar sub-group" consisting of Asn and Gln. The aromatic or cyclic group can be sub-divided into the sub-groups consisting of the "nitrogen ring sub-group," consisting of Pro, His and Trp; and the "phenyl sub-group" consisting of Phe and Tyr. The aliphatic group can be sub-divided into the sub-groups consisting of the "large aliphatic non-polar sub-group," consisting of Val, Leu and Ile; the "aliphatic slightly-polar sub-group," consisting of Met, Ser, Thr and Cys; and the "small-residue sub-group," consisting of Gly and Ala.

Examples of conservative mutations include substitutions of amino acids within the sub-groups above, for example, Lys for Arg and vice versa such that a positive charge can be maintained; Glu for Asp and vice versa such that a negative charge can be maintained; Ser for Thr such that a free —OH can be maintained; and Gln for Asn such that a free —NH$_2$ can be maintained.

Control plant: The term "control plant" refers to a plant without introduced trait-improving recombinant DNA. A control plant is used as a standard against which to measure and compare trait improvement in a transgenic plant comprising such trait-improving recombinant DNA. One suitable type of control plant is a non-transgenic plant of the parental line that was used to generate a transgenic plant, i.e., an otherwise identical wild-type plant. Another type of suitable control plant is a transgenic plant that comprises recombinant DNA without the specific trait-producing DNA, e.g., simply an empty vector.

The terms "enhance", "enhanced", "increase", or "increased" refer to a statistically significant increase. For the avoidance of doubt, these terms generally refer to about a 5% increase in a given parameter or value, about a 10% increase, about a 15% increase, about a 20% increase, about a 25% increase, about a 30% increase, about a 35% increase, about a 40% increase, about a 45% increase, about a 50% increase, about a 55% increase, about a 60% increase, about a 65% increase, about 70% increase, about a 75% increase, about an 80% increase, about an 85% increase, about a 90% increase, about a 95% increase, about a 100% increase, or more over the control value. These terms also encompass ranges consisting of any lower indicated value to any higher indicated value, for example "from about 5% to about 50%", etc.

Food Crop Plant: Plants that are either directly edible, or which produce edible products, and that are customarily used to feed humans either directly, or indirectly through animals. Non-limiting examples of such plants include:

1. Cereal crops: wheat, rice, maize (corn), barley, oats, sorghum, rye, and millet;
2. Protein crops: peanuts, chickpeas, lentils, kidney beans, soybeans, lima beans;
3. Roots and tubers: potatoes, sweet potatoes, and cassavas;
4. Oil crops: corn, soybeans, canola (rapeseed), wheat, peanuts, palm, coconuts, safflower, sesame, cottonseed, sunflower, flax, olive, and safflower;
5. Sugar crops: sugar cane and sugar beets;
6. Fruit crops: bananas, oranges, apples, pears, breadfruit, pineapples, and cherries;
7. Vegetable crops and tubers: tomatoes, lettuce, carrots, melons, asparagus, etc.
8. Nuts: cashews, peanuts, walnuts, pistachio nuts, almonds;
9. Forage and turf grasses;
10. Forage legumes: alfalfa, clover;
11. Drug crops: coffee, cocoa, kola nut, poppy, tobacco;
12. Spice and flavoring crops: vanilla, sage, thyme, anise, saffron, menthol, peppermint, spearmint, coriander The terms "biofuels crops", "energy crops", "oil crops", "oilseed crops", and the like, to which the present methods and compositions can also be applied include the oil crops listed in item 4., above, and further include plants such as sugarcane, castor bean, *Camelina*, switchgrass, *Miscanthus*, and *Jatropha*, which are used, or are being investigated and/or developed, as sources of biofuels due to their significant oil production and accumulation.

Genome: This term can collectively refer to the totality of different genomes within plant cells, i.e., nuclear genome, plastid (especially chloroplast genome), and mitochondrial genome, or separately to the each of these individual genomes when specifically indicated. As used herein, the term "genome" refers to the nuclear genome unless indicated otherwise. The preferred "genome" for expression of the type III Gγ proteins employed in the present recombinant methods and plants is the nuclear genome. However, expression in a plastid genome, e.g., a chloroplast genome, or targeting of a type III Gγ protein to a plastid genome such as a chloroplast via the use of a plastid targeting sequence, is also encompassed by the present invention.

Heterologous: The term "heterologous" refers to a nucleic acid fragment or protein that is foreign to its surroundings. In the context of a nucleic acid fragment, this is typically accomplished by introducing such fragment, derived from one source, into a different host. Heterologous nucleic acid fragments, such as coding sequences that have been inserted into a host organism, are not normally found in the genetic complement of the host organism. As used herein, the term "heterologous" also refers to a nucleic acid fragment derived from the same organism, but which is located in a different, e.g., non-native, location within the genome of this organism. Thus, the organism can have more than the usual number of copy(ies) of such fragment located in its(their) normal position within the genome and in addition, in the case of plant cells, within different genomes within a cell, for example in the nuclear genome and within a plastid or mitochondrial genome as well. A nucleic acid fragment that is heterologous with respect to an organism into which it has been inserted or transferred is sometimes referred to as a "transgene."

A "transgenic" organism, such as a transgenic plant, is a host organism that has been genetically engineered to contain one or more heterologous nucleic acid fragments, including nucleotide coding sequences, expression cassettes, vectors, etc. Introduction of heterologous nucleic acids into a host cell to create a transgenic cell is not limited to any particular mode of delivery, and includes, for example, microinjection, adsorption, electroporation, particle gun bombardment, whiskers-mediated transformation, liposome-mediated delivery, *Agrobacterium*-mediated transfer, the use of viral and retroviral vectors, etc., as is well known to those skilled in the art.

The term "homology" describes a mathematically based comparison of sequence similarities which is used to identify genes or proteins with similar functions or motifs. The nucleic acid and protein sequences of the present invention can be used as a "query sequence" to perform a search against public databases to, for example, identify other family members, related sequences or homologs. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and BLAST) can be used.

The term "homologous" refers to the relationship between two proteins that possess a "common evolutionary origin", including proteins from superfamilies (e.g., the immunoglobulin superfamily) in the same species of animal, as well as homologous proteins from different species of animal (for example, myosin light chain polypeptide, etc.; see Reeck et al., (1987) *Cell*, 50:667). Such proteins (and their encoding nucleic acids) have sequence homology, as reflected by their sequence similarity, whether in terms of percent identity or by the presence of specific residues or motifs and conserved positions.

Ionizing Radiation: High-energy radiation capable of producing ionization in substances through which it passes. This includes nonparticulate radiation, such as x-rays, and radiation produced by energetic charged particles, such as alpha and beta rays, and by neutrons, as from a nuclear reaction. Gamma rays are also included in this class.

Non-Ionizing Radiation: Any type of electromagnetic radiation that does not carry enough energy per quantum to ionize atoms or molecules—that is, to completely remove an electron from an atom or molecule. Instead of producing charged ions when passing through matter, the electromagnetic radiation has sufficient energy only for excitation, the movement of an electron to a higher energy state. Nevertheless, different biological effects are observed for different types of non-ionizing radiation. Near ultraviolet, visible light, infrared, microwave, radio waves, and low-frequency RF (longwave) are all examples of non-ionizing radiation. Visible and near ultraviolet may induce photochemical reactions, ionize some molecules, or accelerate radical reactions.

Oil Crop Plant Oils: Plant (or vegetable) oils are triglycerides obtained from plants. Most, but not all vegetable oils are extracted from seeds or fruits. Edible vegetable oils are used in food, both in cooking and as supplements. In addition, edible and other plant oils are used as biofuels, in cosmetics, for medical purposes, and various industrial purposes. Major classes of oils are:

Edible Oils

Major edible oils include the following, which are also used as fuel oils: coconut oil, corn oil, cottonseed oil, olive oil, palm oil, peanut oil, rapeseed oil, safflower oil, sesame oil, soybean oil, and sunflower oil. Nut oils, which are generally used in cooking, include almond oil, beech nut oil, cashew oil, hazelnut oil, Macadamia oil, Mongongo nut oil, pecan oil, pine nut oil, pistachio oil, and walnut oil. Citrus oils include grapefruit seed oil, lemon oil, and orange oil. Usable oils can be obtained from the seeds of many members of the citrus family.

Melon and gourd seed oils are obtained from members of the Cucurbitaceae, including gourds, melons, pumpkins, and squashes. Examples of such oils include bitter gourd oil from seeds of *Momordica charantia*, bottle gourd oil from seeds of *Lagenaria siceraria*, buffalo gourd oil from seeds of *Cucurbita foetidissima*, butternut squash seed oil from seeds of *Cucurbita moschata*, Egus seed oil from seeds of *Cucumeropsis mannii naudin*, pumpkin seed oil, and watermelon seed oil from seeds of *Citrullus vulgaris*.

Other edible oils include Amaranth oil from the seeds of grain amaranth species, including *Amaranthus cruentus* and *Amaranthus hypochondriacus*; apricot oil; apple seed oil; Argan oil from the seeds of the *Argania spinosa*; avocado oil; babassu oil from the seeds of *Attalea speciosa*; ben oil extracted from the seeds of the *Moringa oleifera*; borneo tallow nut oil extracted from the fruit of species of genus *Shorea*; cape chestnut oil, also called yangu oil; carob pod oil (Algaroba oil); cocoa butter (also known as theobroma oil); cocklebur oil from species of genus *Xanthium*; cohune oil from *Attalea cohune* (cohune palm); coriander seed oil; date seed oil; dika oil from *Irvingia gabonensis* seeds; false flax oil from seeds of *Camelina sativa*; grape seed oil; hemp oil; kapok seed oil from the seeds of *Ceiba pentandra*; kenaf seed oil from the seeds of *Hibiscus cannabinus;* lallemantia oil from the seeds of *Lallemantia iberica*; mafura oil extracted from the seeds of *Trichilia emetica*; manila oil extracted from the kernel of *Sclerocarya birrea*; meadowfoam seed oil; mustard oil; nutmeg butter extracted by expression from the fruit of cogeners of genus *Myristica*; nutmeg oil; okra seed oil from *Abelmoschus esculentus*; papaya seed oil; perilla seed oil; persimmon seed oil extracted from the seeds of *Diospyros virginiana*; pequi oil extracted from the seeds of *Caryocar brasiliense*; pili nut oil extracted from the seeds of *Canarium ovatum*; pomegranate seed oil from *Punica granatum* seeds; poppyseed oil; prune kernel oil; Quinoa oil; ramtil oil pressed from the seeds of the one of several species of genus *Guizotia abyssinica* (Niger pea); rice bran oil; royle oil pressed from the seeds of *Prinsepia utilis*; sacha inchi oil; sapote oil; seje oil from the seeds of *Jessenia bataua*; shea butter; taramira oil from the seeds of arugula (*Eruca sativa*); tea seed oil (Camellia oil); thistle oil pressed from the seeds of *Silybum marianum*; tigernut oil (or nut-sedge oil); tobacco seed oil from the seeds of *Nicotiana tabacum* and other *Nicotiana* species; tomato seed oil; and wheat germ oil.

Edible Oils Used as Food Supplements, or "Nutraceuticals"

Oils used as food supplements, or "nutraceuticals", include Açaï oil, black seed oil pressed from *Nigella sativa* seeds, blackcurrant seed oil from the seeds of *Ribes nigrum*, borage seed oil from the seeds of *Borago officinalis*, evening primrose oil from the seeds of *Oenothera biennis*, and flaxseed oil (called linseed oil when used as a drying oil) from the seeds of *Linum usitatissimum*.

Multipurpose Oils

Oils used primarily for human consumption, but which have been considered for use as biofuels, i.e., multipurpose oils, include: castor oil; coconut oil (copra oil); colza oil from *Brassica rapa*, var. *oleifera* (turnip); corn oil; cottonseed oil; false flax oil from *Camelina sativa*; hemp oil; mustard oil; palm oil; peanut oil; radish oil; rapeseed oil; ramtil oil; rice bran oil; safflower oil; *salicornia* oil from the seeds of *Salicornia bigelovii*; soybean oil; sunflower oil; and tigernut oil.

Inedible Oils Used Only or Primarily as Biofuel

Inedible oils used only or primarily as biofuel and that are extracted from plants cultivated solely for producing oil-based biofuel include: copaiba from species of genus *Copaifera*; honge oil (Pongamia); *Jatropha* oil; Jojoba oil from the *Simmondsia chinensis; milk bush oil; nahor oil pressed from the kernels of Mesua ferrea*; paradise oil from the seeds of *Simarouba glauca*; petroleum nut oil from the Petroleum nut (*Pittosporum resiniferum*); and tung oil.

Drying Oils

Vegetable oils that dry to a hard finish at normal room temperature are referred to as "drying oils", and are used as the basis of oil paints and in other paint and wood finishing applications. Such oils include walnut, sunflower and safflower oil; dammar oil from *Canarium strictum*; linseed (flaxseed) oil; poppyseed oil; stillingia oil (also called Chinese vegetable tallow oil) obtained by solvent from the seeds of *Sapium sebiferum*; tung oil; and *vernonia* oil produced from the seeds of the *Vernonia galamensis*.

Oils Used in Industrial Applications and Commercial Products

Other plant oils of importance that are either inedible, or which are not commonly ingested as edible oils, can be used for a wide variety of other purposes including, for example, insecticides, perfumes, various industrial applications, sources of triglycerides and fatty acids, medicinal and cosmetic uses, etc. These include, for example amur cork tree fruit oil pressed from the fruit of *Phellodendron amurense*; artichoke oil extracted from the seeds of the artichoke fruit; balanos oil pressed from the seeds of *Balanites aegyptiaca*; bladderpod oil pressed from the seeds of *Lesquerella fendleri; brucea javanica* oil extracted from the seeds of the *Brucea javanica*; burdock oil (Bur oil) extracted from the root of the burdock; candlenut oil (Kukui nut oil); carrot seed oil pressed from carrot seeds; castor oil; chaulmoogra oil from seeds of *Hydnocarpus wightiana; crambe* oil extracted from seeds of *Crambe abyssinica; croton* oil (tiglium oil) pressed from seeds of *Croton tiglium; cuphea* oil from a number of species of genus *Cuphea*; honesty oil from seeds of *Lunaria annua*; illipe butter from the nuts of *Shorea stenoptera*; Jojoba oil; mango oil pressed from the stones of the mango fruit; mowrah butter from seeds of *Madhuca latifolia* and *Madhuca longifolia*; neem oil from *Azadirachta indica*; ojon oil extracted from the nut of the American palm (*Elaeis oleifera*); rose hip seed oil; rubber seed oil pressed from the seeds of the rubber tree (*Hevea brasiliensis*); sea buckthorn oil derived from *Hippophae rhamnoides*; sea rocket seed oil from the halophyte *Cakile maritima*; snowball seed oil (*Viburnum* oil) from *Viburnum opulus* seeds; tall oil and tall oil fatty acid (TOFA) produced as byproducts of wood pulp manufacture; tamanu or foraha oil from *Calophyllum tacamahaca*; tonka bean oil (Cumaru oil); and ucuhuba seed oil extracted from seeds of *Virola surinamensis*.

Operably linked: As used herein "operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence. Similarly, "control elements compatible with expression in a subject" are those that are capable of effecting the expression of the coding sequence in that subject.

Recombinant DNA: As used herein "recombinant DNA" means a DNA molecule having a genetically engineered modification introduced through a combination of endogenous and/or exogenous DNA elements in a transcription unit, manipulation via mutagenesis, restriction enzymes, and the like, or simply by inserting multiple copies of a native transcription unit. Recombinant DNA may comprise DNA segments obtained from different sources, or DNA segments obtained from the same source, but which have been manipulated to join DNA segments which do not naturally exist in the joined form. Recombinant DNA can exist outside of a cell, e.g., as a PCR fragment or in a plasmid, or can be integrated into a genome such as a plant genome.

Redox Stress: This refers to a generic stress signal transduction pathway initiated by signal perception, followed by the generation of second messengers (e.g., inositol phosphates and reactive oxygen species). Within a cell, the presence of second messengers may trigger the antioxidant defense system through a protein phosphorylation cascade that targets proteins directly involved in cellular protection or transcription factors controlling specific sets of stress-regulated genes.

For example, when plants are exposed to unfavorable high growing temperatures, normal protein synthesis is reduced and rapid synthesis of heat shock proteins begins. Similarly, low temperature acclimation in plants is associated with the synthesis of hydrophilic proteins that act as cryoprotectants. Many plants respond to stress by accumulating high levels of proteins believed to protect plant tissues from osmotic stress. However, if the severity and duration of these stress conditions are intense or persist for a prolonged period, the deleterious effects on plant development, growth, and yield of most crop plants are significant. Continuous exposure to stresses causes major alterations in plant metabolism. These metabolic perturbations ultimately lead to cell death, visible injury, loss of membrane integrity, dramatically reduced rates of photosynthesis, increased ethylene production, premature senescence, and consequent yield losses.

Redox stresses result from conditions that promote the formation of reactive oxygen species, producing an excess of free radicals that damage or kill cells. Free radicals are essential for plant growth and development, and under normal circumstances, there is a balance between reductive and oxidative compounds (redox state) inside the cell. If the balance is in favor of either oxidative or reductive compounds, redox stress is said to occur. Agents that induce redox stresses in plants include cold, drought, flood, heat, ionizing and non-ionizing radiation, including UV stress, ozone increases, increased sulfur dioxide, acid rain, air/water/soil pollutants, salt stress, heavy metals, mineralized soils, pesticides, herbicides such as paraquat dichloride (methyl viologen, 1,1'-dimethyl-4,4'-bipyridinium), free radical scavengers such as dithiothreitol (DTT) and reduced gluthathione (GSH), as well as other abiotic stresses.

Transgenic plant: As used herein, the term "transgenic plant" means a plant produced from an original transformation event employing a recombinant DNA molecule, usually a nucleotide coding sequence, as well as progeny of such original transformation event obtained sexually or asexually, for example via seed or asexual reproduction using cuttings, tissue culture, etc., of such original transformation event plant, or progeny from subsequent generations or crosses of a plant to a transformed plant, so long as the progeny contains a copy of the original recombinant DNA introduced via the original transformation event in its genome.

General Methods

Practice of the present invention employs, unless otherwise indicated, conventional techniques of molecular biology, recombinant DNA technology, microbiology, chemistry, etc., which are well known in the art and within the capabilities of those of ordinary skill in the art. Such techniques include the following non-limiting examples: preparation of cellular, plasmid, and bacteriophage DNA; manipulation of purified DNA using nucleases, ligases, polymerases, and DNA-modifying enzymes; introduction of DNA into living cells; cloning vectors for various organisms; PCR; gene deletion, modification, replacement, or inhibition; production of recombinant peptides, polypeptides, and proteins in host cells; chromatographic methods; etc.

Such methods are well known in the art and are described, for example, in Green and Sambrook (2012) *Molecular Cloning: A Laboratory Manual*, Fourth Edition, Cold Spring Harbor Laboratory Press; Ausubel et al. (2003 and periodic supplements) *Current Protocols in Molecular Biology*, John Wiley & Sons, New York, N.Y.; Amberg et al. (2005) *Methods in Yeast Genetics: A Cold Spring Harbor Laboratory Course Manual*, 2005 Edition, Cold Spring Harbor Laboratory Press; Roe et al. (1996) *DNA Isolation and Sequencing: Essential Techniques*, John Wiley & Sons; J. M. Polak and James O'D. McGee (1990) *In Situ Hybridization: Principles and Practice*; Oxford University Press; M. J. Gait (Editor) (1984) *Oligonucleotide Synthesis: A Practical Approach*, IRL Press; D. M. J. Lilley and J. E. Dahlberg (1992) *Methods in Enzymology: DNA Structure Part A: Synthesis and Physical Analysis of DNA*, Academic Press; and *Lab Ref: A Handbook of Recipes, Reagents, and Other Reference Tools for Use at the Bench*, Edited by Jane Roskams and Linda Rodgers (2002) Cold Spring Harbor Laboratory Press; Burgess and Deutscher (2009) *Guide to Protein Purification*, Second Edition (*Methods in Enzymology*, Vol. 463), Academic Press. Note also U.S. Pat. Nos. 8,178,339; 8,119,365; 8,043,842; 8,039,243; 7,303,906; 6,989,265; US20120219994A1; and EP1483367B1. The entire contents of each of these texts and patent documents is herein incorporated by reference.

Type III Gγ Proteins

The AGG3 gene was originally characterized in *Arabidopsis* for its role in regulation of ABA-mediated signaling pathways (Chakravorty et al., 2011).

*Arabidopsis* AGG3 (AT5G20635) is a novel heterotrimeric G-protein γ subunit involved in guard cell K$^+$-channel regulation, morphological development, and control of organ shape and size (Chakravorty et al., 2011; Li et al., 2012). Sequence homologs of AGG3 are present in angiosperms and gymnosperms, but not in other organisms (Trusov et al., 2012). Analysis of the recently available *C. sativa* sequence database (Liang et al., 2013) revealed the existence of a homologue of this *Arabidopsis* protein that shows extremely high sequence similarity with AGG3. It is fully expected that these and other sequence homologs of *Arabidopsis* AGG3, and their encoding nucleic acids, will be useful in the present methods and transgenic plants in view of their shared structure, and therefore function.

The homologs of type III Gγ proteins have been proposed to be major regulators of yield-related traits such as seed size, seed number, panicle branching, and abiotic stress tolerance based on studies in *Arabidopsis*, rice, and soybean (Chakravorty et al., 2011; Fan et al., 2009; Huang et al., 2009; Li et al., 2012; Roy Choudhury and Pandey, 2013). While the *Arabidopsis* data are relatively straightforward, the markedly small size of *Arabidopsis* seeds and relative modest phenotypes necessitate their further evaluation. The rice data, on the other hand, are fairly complex. Specific mutations that allow for the expression of different truncated versions of the same protein lead to distinct, sometimes contrasting phenotypes (Botella, 2012; Lu and Kang, 2008; Mao et al., 2010). Therefore, further studies are required to establish the potential positive effects of type III Gγ genes and to expand their scope on agronomically important plants. In this work, we chose to investigate the potential of the *Arabidopsis* AGG3 gene in *C. sativa* because it is an emerging biofuel crop that is closely related to the model plant *A. thaliana*. Importantly, its larger plant stature and seed size facilitate detailed quantitative evaluation of various biomass and seed-associated traits. We used a constitutive CaMV35S promoter, as well as a seed-specific glycinin promoter (FIG. 1), for expression of AGG3 in transgenic *Camelina*. A seed-specific promoter was used to minimize any potential deleterious effects of high-level constitutive expression of AGG3 gene from a constitutive promoter.

Engineering stress tolerance is an important aspect of overall plant productivity (Carmo-Silva and Salvucci, 2012; Parry and Hawkesford, 2012; Rojas et al., 2010). Interestingly, the AGG3 gene in *Arabidopsis* was initially identified as the missing piece of the G-protein heterotrimer that regulates ABA signaling in conjunction with the Gα and Gβ proteins (Chakravorty et al., 2011). The previously identified Gγ proteins of *Arabidopsis*, AGG1 and AGG2, are not involved in the regulation of ABA signaling, but do mediate biotic stress responses of plants (Chakravorty et al., 2011; Thung et al., 2012; Trusov et al., 2008).

As per the established signaling mechanisms, Gγ proteins always act as obligate dimers with Gβ proteins. While the exact number of subunits of each G-protein remains to be identified in *Camelina*, it is conceivable that additional Gγ proteins are present in the *Camelina* genome based on the subunit diversity and its relationship to plant ploidy (Bisht et al., 2011; Roy Choudhury et al., 2011; Trusov et al., 2012). It is therefore possible that by overexpressing the Gγ subunit alone, the quantity of Gβ protein becomes limited and/or the stoichiometry between different Gβγ combinations is affected.

Type III Gγ protein sequences (and their encoding nucleic acids) encompassed by the present invention include not only those specifically disclosed herein, but also sequences having sequence identities of at least 80%, at least 85%, at least 90%, at least 95%, at least 96%, at least 97%, at least 98%, or at least 99% sequence identity to a type III Gγ protein sequence disclosed herein. Alternatively, type III Gγ protein sequences encompassed by the present invention include not only those specifically disclosed herein, but also sequences having 1, 2, 3, 4, or 5 amino acid changes at corresponding positions compared to type III Gγ protein sequences disclosed herein. Such sequence identical, or amino acid modified, type III Gγ proteins should exhibit at least about ±25% of the biochemical/physiological activity of the corresponding specific type III Gγ protein sequence (*Arabidopsis* AGG3) disclosed herein, as determined, for example, by the methods disclosed in the examples below.

As used herein, the phrase "sequence identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., *SIAM J. Applied Math.*, 48: 1073 (1988). Methods to determine identity are designed to give the largest match between the sequences tested. Moreover, methods to determine identity are codified in publicly available computer programs.

Optimal alignment of sequences for comparison can be conducted, for example, by the local homology algorithm of Smith & Waterman, by the homology alignment algorithms, by the search for similarity method or, by computerized implementations of these algorithms (GAP, BESTFIT, PASTA, and TFASTA in the GCG Wisconsin Package, available from Accelrys, Inc., San Diego, Calif., United States of America), or by visual inspection. See generally, (Altschul, S. F. et al., *J. Mol. Biol.* 215: 403-410 (1990) and Altschul et al. *Nucl. Acids Res.* 25: 3389-3402 (1997)).

One example of an algorithm that is suitable for determining percent sequence identity and sequence similarity is the BLAST algorithm, which is described in (Altschul, S., et al., NCBI NLM NIH Bethesda, Md. 20894; & Altschul, S., et al., *J. Mol. Biol.* 215: 403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold.

These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always; 0) and N (penalty score for mismatching residues; always; 0). For amino acid sequences, a scoring matrix is used to calculate the cumulative score. Extension of the word hits in each direction are halted when: the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is in one embodiment less than about 0.1, in another embodiment less than about 0.01, and in still another embodiment less than about 0.001.

It should be noted that the nucleotide and amino acid sequences useful in the methods and plants of the present invention can comprise, consist essentially of, or consist of, the specific sequences disclosed herein.

Promoters

A variety of different promoters can be used in the practice of the present invention depending upon the desired location of type III Gγ protein expression within a plant, level of expression, timing of expression, developmental stage of expression, response to environmental stimuli, etc. The following are representative non-limiting examples of promoters that can be used in the expression cassettes of the present invention.

Constitutive Promoters:

Constitutive promoters typically provide for the constant and substantially uniform production of proteins in all tissues. For example, the promoter can be a viral promoter such as a CaMV35S or FMV35S promoter. The CaMV35S and FMV35S promoters are active in a variety of transformed plant tissues and most plant organs (e.g., callus, leaf, seed, and root). Enhanced or duplicate versions of the CaMV35S and FMV35S promoters are particularly useful in the practice of this invention (U.S. Pat. No. 5,378,619, incorporated herein by reference in its entirety). Other useful promoters include the nopaline synthase (NOS) and octopine synthase (OCS) promoters (which are carried on tumor-inducing plasmids of *A. tumefaciens*), the cauliflower mosaic virus (CaMV) 19S promoters, a maize ubiquitin promoter, the rice Act1 promoter, and the Figwort Mosaic Virus (FMV) 35S promoter (see, e.g., U.S. Pat. No. 5,463,175, incorporated herein by reference in its entirety).

Other exemplary constitutive promoters include, for example, the core promoter of the Rsyn7 (U.S. patent application Ser. No. 08/661,601), the core CaMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. patent application Ser. No. 08/409,297), and the like. Other constitutive promoters include, for example, those disclosed in U.S. Pat. Nos. 5,608,149; 5,608,144; 5,604,121; 5,569,597; 5,466,785; 5,399,680; 5,268,463; and 5,608,142.

Tissue-Specific Promoters:

Promoters that are active in certain plant tissues (i.e., tissue-specific promoters) can also be used to drive expression of type III Gγ proteins. Depending on the redox stress, and tissue susceptibility to such stress, to which protection is sought, the present type III Gγ proteins can be expressed in any tissue or organ in the plant where the redox stress is most damaging. For example, in the case of redox stress caused by an air pollutant, ionizing or non-ionizing radiation, or a foliar pesticide, a preferred site for expression is in the leaves and stems. In the case of redox stress caused by a soil pollutant, a preferred site for expression is in roots. In any of these situations, expression in particular tissues can be achieved via the use of tissue-specific promoters. Promoters active at particular developmental stages in the plant life cycle can be used to optimize resistance to redox stress when it is most needed.

Expression of type III Gγ proteins in the tissue that is typically adversely affected by a redox stress is anticipated to be particularly useful, as are promoters specific to plant tissues and organs in which oils are produced and accumulated. Thus, expression in reproductive tissues, seeds, roots, stems, or leaves can be particularly useful in enhancing resistance of plant parts particularly susceptible to a redox stress in certain crops, or oil accumulation therein.

Examples of useful tissue-specific, developmentally regulated promoters include, but are not limited to, the β-conglycinin 7S promoter (Doyle et al., 1986), seed-specific promoters (Lam and Chua, 1991), and promoters associated with napin, phaseolin, zein, soybean trypsin inhibitor, ACP, stearoyl-ACP desaturase, or oleosin genes. Tissue-specific promoters also include those described in Yamamoto et al. (1997) Plant J. 12(2):255-265; Kawamata et al. (1997) Plant Cell Physiol. 38(7):792-803; Hansen et al. (1997) Mol. Gen. Genet. 254(3):337-343; Russell et al. (1997) Transgenic Res. 6(2):157-168; Rinehart et al. (1996) Plant Physiol. 112(3):1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20:181-196; Orozco et al. (1993) Plant Mol. Biol. 23(6): 1129-1138; Matsuoka et al. (1993) Proc. Natl. Acad. Sci. U.S.A. 90(20):9586-9590; and Guevara-Garcia et al. (1993) Plant J. 4(3):495-505.

Examples of root-specific promoters include, but are not limited to, the RB7 and RD2 promoters described in U.S. Pat. Nos. 5,459,252 and 5,837,876, respectively. Root specific promoters also include, for example, those disclosed in Hire, et al (1992) Plant Mol. Biology, 20(2): 207-218; Keller and Baumgartner, (1991) The Plant Cell, 3(10): 1051-1061; Sanger et al. (1990) Plant Mol. Biology, 14(3): 433-443; Miao et al. (1991) The Plant Cell, 3(1): 11-22; Bogusz et al. (1990) The Plant Cell, 2(7): 633-641.

Seed-preferred promoters includes both seed-specific promoters (those promoters active during seed development) as well as seed-germinating promoters (those promoters active during seed germination). Such promoters include beta conglycinin, (Fujiwara & Beachy (1994) Plant. Mol. Biol. 24 261-272); Cim1 (cytokinin-induced message); cZ19B1 (maize 19 KDa zein); milps (myo-inositol-1-phosphate synthase); celA (cellulose synthase); end1 (Hordeum verlgase mRNA clone END1); and imp3 (myo-inositol monophosphate-3). For dicots, particular promoters include phaseolin, napin, β-conglycinin, soybean lectin, and the like. For monocots, particular promoters include maize 15 Kd zein, 22 KD zein, 27 kD zein, waxy, shrunken 1, shrunken 2, globulin 1, etc. In certain embodiments the DNA constructs, transgenic plants and methods use the oleosin promoter and/or napin promoter.

Promoters Induced by Environmental Stimuli:

Another class of useful promoters are promoters that are induced by various environmental stimuli. Promoters that are induced by environmental stimuli include, but are not limited to, promoters induced by heat (e.g., heat shock promoters such as Hsp70), promoters induced by light (e.g., the light-inducible promoter from the small subunit of ribulose 1,5-bisphosphate carboxylase, ssRUBISCO, a very abundant plant polypeptide), promoters induced by cold (e.g., COR promoters), promoters induced by oxidative stress (e.g., catalase promoters), promoters induced by drought (e.g., the wheat Em and rice rab16A promoters), and promoters induced by multiple environmental signals (e.g., rd29A promoters, Glutathione-S-transferase (GST) promoters).

Chemically Inducible Promoters:

A chemically induced promoter element can be used to replace, or in combination with any of the foregoing promoters to enable the chemically inducible expression of type III Gγ protein throughout a plant, or within a specific tissue. For example the expression of trans factor comprising the ecdysone receptor operatively coupled to a GAL4 DNA binding domain and VP16 activation domain can be used to regulate the expression of a second gene that is operatively coupled to a minimal promoter and GAL4 (5×UAS sequences) in a ligand depend fashion. A number of useful EcRs are known in the art, and have been used to develop ligand regulated gene switches. Specific examples of EcR based gene switches include for example those disclosed in U.S. Pat. Nos. U.S. Pat. Nos. 6,723,531, 5,514,578, 6,245, 531, 6,504,082, 7,151,168, 7,205,455, 7,238,859, 7,456,315, 7,563,928, 7,091,038, 7,531,326, 7,776,587, 7,807,417, 7,601,508, 7,829,676, 7,919,269, 7,563,879, 7,297,781, 7,312,322, 6,379,945, 6,610,828, 7,183,061 and 7,935,510. In addition, other chemical regulators can also be employed to induce expression of the selected coding sequence in the plants transformed according to the presently disclosed subject matter, including the benzothiadiazole, isonicotinic acid, salicylic acid, for example as disclosed in U.S. Pat. Nos. 5,523,311, 5,614,395, and 5,880,333 herein incorporated by reference.

The promoter of choice is preferably excised from its source by restriction enzymes, but can alternatively be PCR-amplified using primers that carry appropriate terminal restriction sites.

It should be understood that the foregoing groups of exemplary promoters are non-limiting, and that one skilled in the art could employ other promoters that are not explicitly cited here in the practice of this invention.

Overview

The present invention includes DNA constructs and methods for producing transgenic plants that exhibit enhanced resistance to redox stresses of various kinds, as well as enhanced oil production. In one aspect, such transgenic plants are created through the expression, or overexpression, of a type III Gγ protein, for example AGG3. Such proteins can be expressed in any tissue or organ of a plant, using a wide variety of different types of promoters, to achieve the desired effect in the desired location at the desired time in the plant life cycle. In the case of oilseed crops plants, it may be desirable to express such proteins under the control of a promoter specific to the tissue in which oil is normally produced and accumulated, for example a seed-specific or fruit-specific promoter.

Also envisaged within the present invention is the use of cells and tissues of the transgenic plants disclosed herein in suspension cultures and tissue cultures, respectively, to produce desirable oils by in vitro cultivation.

Type III Gγ Protein Nucleotide and Amino Acid Sequences

Expression of nucleotide sequences encoding type III Gγ proteins such as AGG3 in the present methods can be optimized by including consensus sequences at and around the start codon. Such codon optimization can be completed by standard analysis of the preferred codon usage for the host plant in question, and the synthesis of an optimized nucleic acid via standard DNA synthesis. Codon usage in various monocot and dicot genes has been disclosed in Akira Kawabe and Naohiko T. Miyashita, "Patterns of codon usage bias in three dicot and four monocot plant species" *Genes Genet. Syst.* 78 343-352 (2003) and E. E. Murray et al. "Codon Usage in Plant Genes" *NAR* 17:477-498 (1989). A number of companies provide such services on a fee for services basis and include for example, DNA2.0, (CA, USA) and Operon Technologies. (CA, USA).

The type III Gγ proteins used in any of the methods and plants of the present invention can have amino acid sequences that are substantially homologous, or substantially similar to, any of the native type III Gγ protein amino acid sequences, for example, to any of the native type III Gγ proteins amino acid sequences encoded by the nucleotide sequences disclosed herein. Table 1 below, adapted from Trusov et al. (2012), lists GenBank accession numbers for known AGG3 homologs.

TABLE 1

| Species and GenBank Number for Known AGG3 homologs | |
|---|---|
| Cycas rumphii | DR061731 |
| Zamia furfuracea | CB095456 |
| Picea sitchensis | DR533730 |
| Picea glauca | DR579171 |
| Arabidopsis thaliana | BT015160 |
| Brassica rapa | AC189411 |
| Aquilegia Formosa | DT735500 |
| Glycine max | CX701891 |
| Medicago truncatula | AC169626 |
| Glycine max | FG994755 + BT095007 |
| Medicago truncatula | AC202480 |
| Populus trichocarpa | DT488475 |
| Solanum lycopersicum | BI210240 |
| Solanum tuberosum | BQ116994 |
| Centaurea maculosa | EH739324 |
| Raphanus raphanistrum | FD976826 + FD981034 |
| Gossypium raimondii | CO121496 + CO121497 |
| Vitis vinifera | AM427921 |
| Beta vulgaris | FG344262 |
| Curcuma longa | DY386604 |
| Zingiber officinale | DY350004 |
| Elaeis guineensis | EL690747 |
| Cenchrus ciliaris | EB660797 + EB671123 |
| Sorghum bicolor | XM_002465107 |
| Zea mays | NM_001151000 |
| Oryza sativa | CT835094 |
| Sorghum bicolor | XM_002444424 |
| Saccharum officinarum | CA230676 + CA230756 |
| Zea mays | EU976637 |
| Triticum aestivum | CJ638838 + CJ666924 |
| Sorghum bicolor | XM_002460230 |
| Zea mays | NM_001158725 |
| Phyllostachys edulis | FP100709 |
| Oryza sativa | NM_001069822 |

Alternatively, the type III Gγ protein may have an amino acid sequence having at least 30%, preferably at least 40, 50, 60, 70, 75, 80, 85, 90, 95, 96, 97, 98, or 99% identity to a type III Gγ protein encoded by a nucleotide disclosed herein. In a preferred embodiment, the type III Gγ protein for use in any of the methods and plants of the present invention is at least 80% identical to the mature AGG3 type III Gγ protein from *Arabidopsis thaliana* (SEQ ID NO:3).

It is known in the art to synthetically modify the sequences of proteins or peptides, while retaining their useful activity, and this can be achieved using techniques that are standard in the art and widely described in the literature, e.g., random or site-directed mutagenesis, cleavage, and ligation of nucleic acids, or via the chemical synthesis or modification of amino acids or polypeptide chains. For instance, conservative amino acid mutations can be introduced into the type III Gγ protein and are considered within the scope of the present invention. Mutations of type III Gγ proteins such as AGG3 homologs in rice that result in changes in seed size, seed length, and panicle branching are known (Fan et al., 2009; Huang et al., 2009; Mao et al., 2010), and other mutations that increase the activity of these proteins can be determined experimentally, and can be used in the methods and plants of the present invention. The type III Gγ proteins such as AGG3 can thus include one or more amino acid deletions, additions, insertions, and/or substitutions based on any of the naturally-occurring isoforms of AGG3. These may be contiguous or non-contiguous. Such variants can include those having 1 to 8, or more preferably 1 to 4, 1 to 3, or 1 or 2 amino acid substitutions, insertions, and/or deletions as compared to any of the sequences disclosed herein.

The variants, derivatives, and fusion proteins of type III Gγ proteins are functionally equivalent in that they have detectable type III Gγ protein activity. Preferably, they exhibit at least 30%, at least 40%, at least 50%, at least 60%, at least 70%, at least 80%, at least 90%, or at least 95% or more of the activity of type III Gγ protein AGG3 from *Arabidopsis thaliana* as determined by the methods in the examples below, and are thus capable of substituting for AGG3 type III Gγ protein from *Arabidopsis* in the present methods and transgenic plants.

All such variants, derivatives, fusion proteins, or fragments of type III Gγ proteins are encompassed by the present invention, and can be used in any of the polynucleotides, expression cassettes, vectors, host cells, and methods disclosed and/or claimed herein, and are subsumed under the term "type III Gγ protein".

Plant Transformation

Techniques for transforming a wide variety of plant species are well known and described in the technical and scientific literature. See, for example, Weising et al, (1988) *Ann. Rev. Genet.*, 22:421-477. As described herein, the DNA constructs of the present invention typically contain a marker gene which confers a selectable phenotype on the plant cells. For example, the marker may encode biocide resistance, particularly antibiotic resistance, such as resistance to kanamycin, G418, bleomycin, hygromycin, or herbicide resistance, such as resistance to chlorsulfuron or Basta®. Such selective marker genes are useful in protocols for the production of transgenic plants.

DNA constructs can be introduced into the genome of the desired plant host by a variety of conventional techniques. For example, the DNA construct may be introduced directly into the plant cell using techniques such as electroporation and microinjection of plant cell protoplasts. Alternatively, the DNA constructs can be introduced directly to plant tissue using biolistic methods, such as DNA micro-particle bombardment. In addition, the DNA constructs may be combined with suitable transfer DNA (T-DNA) flanking regions and introduced into a conventional *Agrobacterium tumefaciens* Ti Plasmid. The T-DNA of the Ti plasmid will be transferred into plant cell through *Agrobacterium*-mediated transformation system.

The following examples are provided to illustrate various aspects of the present invention, and should not be construed as limiting the invention only to these particularly disclosed embodiments. The materials and methods employed in the examples below are for illustrative purposes, and are not intended to limit the practice of the present invention thereto. Any materials and methods similar or equivalent to those described herein can be used in the practice or testing of the present invention.

Example 1

Generation of Constructs for Overexpressing *Arabidopsis* AGG3 in *Camelina*

Figure 1B:
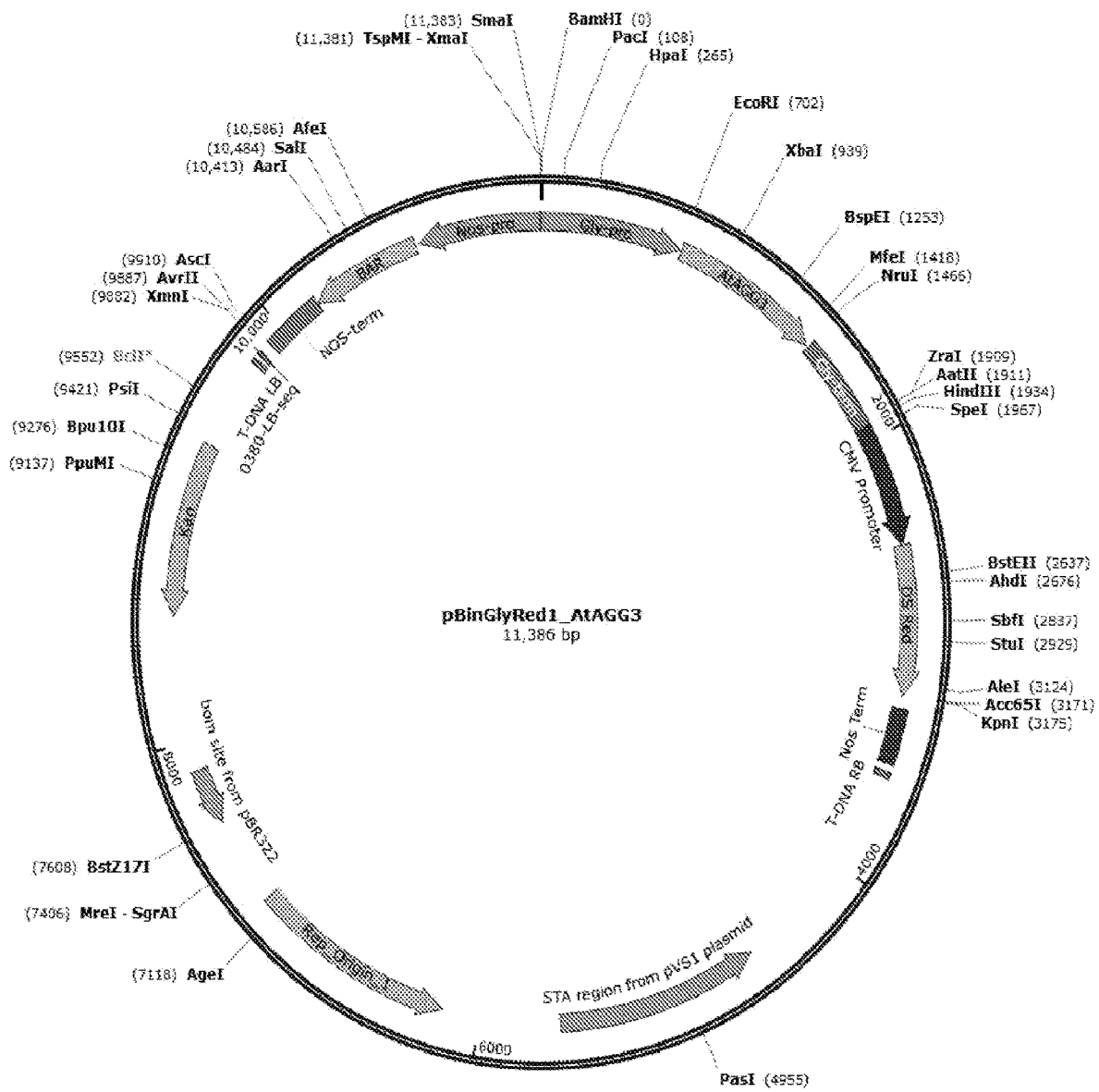

To evaluate the role of *Arabidopsis thaliana* AGG3 in conferring increased stress resistance, biomass production, and higher seed yield, transgenic *Camelina* (*Camelina sativa*, variety Suneson) plants were generated using two types of constructs: CaMV35S:AGG3, expressing *Arabidopsis thaliana* AGG3 cDNA (SEQ ID NO:1) with a constitutive CaMV35S promoter (FIG. 1A), and Glycinin:AGG3, expressing *Arabidopsis thaliana* AGG3 cDNA (SEQ ID NO:1) with a seed-specific, strong soybean glycinin promoter (FIG. 1B). The constructs also included a DsRed reporter gene for visual selection of transgenic seeds, and a Bar gene for Basta® resistance in transgenic plants (e.g., a nucleotide sequence encoding a phosphinothricin acetyltransferase enzyme which upon expression confers resistance to the herbicide glufosinate-ammonium "Basta®").

For *Camelina* transformation, full-length *Arabidopsis thaliana* AGG3 cDNA (SEQ ID NO:1) was amplified using Platinum® Pfx (Invitrogen) from *Arabidopsis* flower cDNA and confirmed by sequencing. The oligonucleotides used for PCR are listed in Table 2. The seed-specific overexpression construct was generated by insertion of AGG3 cDNA into a modified pBinGlyRed1 vector between glycinin promoter and terminator at EcoRI and NruI sites. The constitutive overexpression construct was generated by replacing the glycinin promoter of pBinGlyRed1 vector with CaMV35S promoter at BamHI and EcoRI sites. The expression constructs and empty vectors were introduced into *Agrobacterium tumaefaciens* strain GV301 by electroporation.

Six-week old wild-type *Camelina* plants were transformed with CaMV35S:AGG3, Glycinin:AGG3, and empty vectors using floral dip (Lu and Kang, 2008) followed by a second round of transformation after two weeks to improve the transformation efficiency. Transgenic seeds (T1) were visually selected by Ds-Red expression and transferred to soil for growth to maturity. Seeds from lines displaying a 3:1 segregation of T2 transgenic seeds on the basis of Ds-Red signal were isolated, selfed, and grown to homozygosity. Homozygous T3 seeds of the transgenic plants were selected, and three independent transgenic lines exhibiting maximum expression of the AtAGG3 gene were selfed and used for further analyses.

Seeds of wild-type and transgenic *Camelina* (*Camelina sativa*, variety Suneson) lines were sterilized in 70% ethanol, 30% bleach. and 0.1% Triton-X100 (4-{1,1,3,3-Tetramethylbutyl}phenyl-polyethylene glycol, t-Octylphenoxypolyethoxyethanol, Polyethylene glycol tert-octylphenyl ether) for 30 min by vigorous shaking, followed by extensive washing with sterile water, and transferred on 0.5× Murashige & Skoog (pH 5.7), 1% agar, 1% sucrose medium. The plates were stored for 48 h at 4° C. for stratification. Seeds were germinated at 16 h light, 8 h dark, 23° C. regime in growth chambers. After 4-6 days, the seedlings were transferred to soil-rite (Fafard 3B mix) and grown in the greenhouse (16 h light, 8 h dark, 23° C.).

To evaluate the effect of AGG3 overexpression on different biomass-related traits, twenty-four plants from each transgenic line and from the empty vector (EV) control line were grown side-by-side, and data were recorded for various growth parameters every 2-3 days until the plants reached maturity (10 weeks). The entire experiment was repeated twice, with different batches of seeds and at different times of the year.

TABLE 2

| PCR Primers Primer | Sequence |
| --- | --- |
| AtAGG3FP-forward primer used for amplification of cDNA from plant tissue | 5'-ATGTCTGCTCCTTCTGGCGGTGGCG-3' (SEQ ID NO: 4) |
| AtAGG3RP-reverse primer used for amplification of cDNA from plant tissue | 5'-TTAGAAAGCTAAACAACAAGGATTAG-3' (SEQ ID NO: 5) |
| AtAGG3FP EcoRI-forward primer used for introducing EcoRI site to clone AGG3 in pBinGlyRed1 vector between glycinin promoter and terminator | 5'-ATGCGAATTCATGTCTGCTCCTTCTGGCGGT-3' (SEQ ID NO: 6) |
| AtAGG3RP NruI-reverse primer used for introducing NruI site to clone AGG3 in pBinGlyRed1 vector between glycinin promoter and terminator | 5'-ATGCTCGCGATTAGAAAGCTAAACAACA-3' (SEQ ID NO: 7) |

Example 2

Generation of Transgenic *Camelina* Plants Overexpressing *Arabidopsis* AGG3

As *Camelina sativa* is being developed as a model for herbaceous bioenergy crops and genetic improvement of biomass yield as a major target trait, in addition to higher oil production (Ghamkhar et al., 2010; Nguyen et al., 2013), it was selected as a model system for the experiments described herein.

Figure 2:
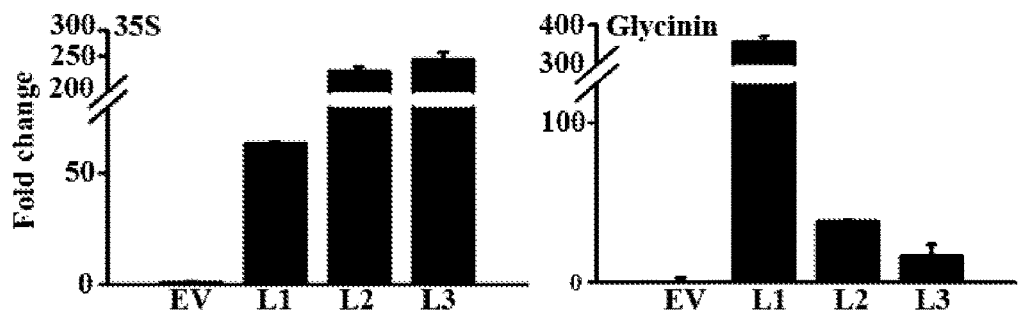
FIG. 2 shows quantitative real-time PCR analyses of AGG3 expression levels in 3-day old seedlings of CaMV35S:AGG3 transgenic *Camelina* lines and in the seeds of Glycinin:AGG3 transgenic *Camelina* lines. The expression was normalized to Actin gene and data presented are mean values of three biological replicates. Error bars represent standard errors (±SE). Expression in empty vector lines (EV) is set at 1.

The T3 homozygous lines were analyzed for increased levels of transgene expression by qRT-PCR in the seedlings of CaMV35S:AGG3 lines and in the seeds of Glycinin:AGG3 plants, and compared to plants containing respective empty vectors (EV control). RNA was isolated from *Arabidopsis* and *Camelina* tissues using TRIzol® RNA (Life technologies) and 1st strand cDNA was prepared by SuperScript® III First-Strand Synthesis System (Invitrogen). Quantitative real-time PCR were performed as described previously (Bisht et al., 2011). The oligonucleotides used for real-time PCR are listed in Table 3. Experiments were repeated three times and data were averaged. Three independent CaMV35S:AGG3 transgenic lines showing ~63-, 219- and 243-fold higher expression levels compared to the CaMV35S empty vector (35S:EV) line, and three independent Glycinin:AGG3 lines showing ~350-, 38- and 16-fold higher expression levels compared to the glycinin empty vector (Glycinin:EV) (FIG. 2) were selected, and the progeny of these seeds were used for further phenotypic analyses as described in the examples below.

TABLE 3

| Real-time PCR Primers Primer | Sequence |
|---|---|
| AtAGG3FPRt1-forward primer used for real time quantitative RT-PCR | 5'-CTTGCTCCGTCGTCTCTACC-3' (SEQ ID NO: 8) |
| AtAGG3RPRt1-reverse primerused for real time quantitative RT-PCR | 5'-GCATCTAGATGCCGGTTGTA-3' (SEQ ID NO: 9) |

Example 3

Overexpression of AGG3 in *Camelina* Results in Higher Seed Oil Content on Per Plant Basis Improvement of seed yield and oil content are the key targets for the biotechnological modification of oilseed crops. Mutations in the AGG3 homologs in rice result in changes in seed size, seed length, and panicle branching (Fan et al., 2009; Huang et al., 2009; Mao et al., 2010). Similarly, changes in expression of the AGG3 gene in *Arabidopsis* by T-DNA knockout or overexpression leads to altered flower and seed sizes (Chakravorty et al., 2011; Li et al., 2012). However, whether such changes in seed size have any effect on the overall seed composition, seed viability, or carbon partitioning has not been evaluated to date. This example was designed to investigate the effect of AGG3 overexpression in the oilseed crop *Camelina*.

Transgenic seeds obtained from transgenic plants prepared as described above in Example 2 were evaluated for their oil quantity per seed, per plant, and for oil composition.

Fatty acid methyl esters (FAME) were prepared from mature *Camelina* seeds essentially according to (Lu et al., 2013). Tri-17:0 triacylglycerol was included as an internal standard. FAME analyses were performed by gas chromatography (Trace GC, ThermoQuest) on a HP-INNOWAX (Agilent technologies) column (30 m×0.25 mm i.d., 0.25 µm film thickness) using helium gas, equipped with a flame ionization detector (AI/AS 3000) injector. Identification of the methyl esters was made by comparison of reaction times of standard fatty acid methyl esters, and a normalization technique was used for quantitation with ChromQuest 5.0, version 3.2.1 (Thermofisher Scientific Inc.). Six plants of each line were used for FAME measurements, and the experiment was repeated twice.

Figure 3:
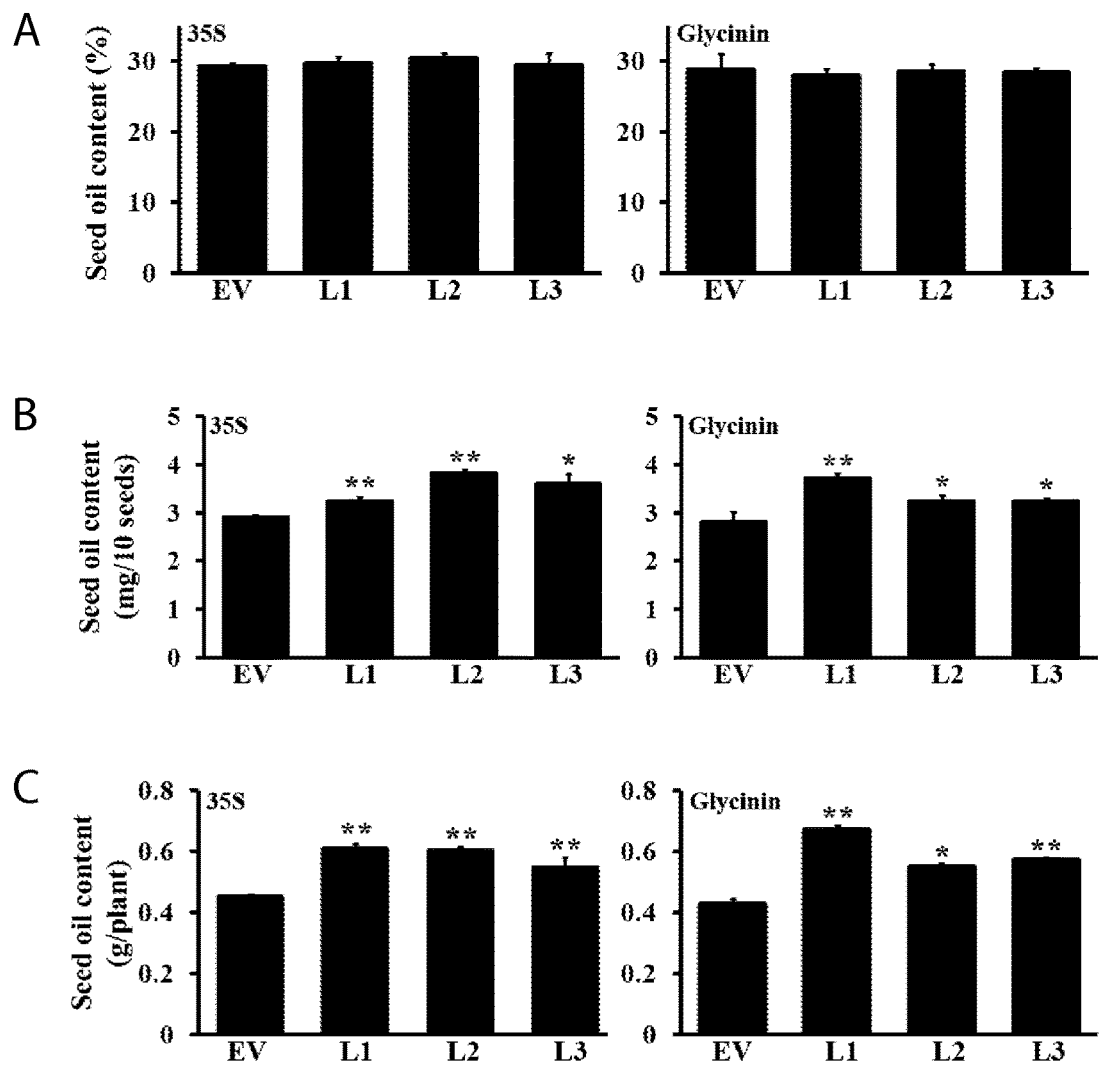
FIG. 3 shows the measurement of oil content in transgenic *Camelina* plants. FAME was extracted from EV and transgenic *Camelina* seeds and analyzed using gas chromatography. (a) Seed oil content (percentage of oil/seed) and (b) Mass of oil/10 seeds were measured in different overexpression lines and compared with their respective EV control. Six biological replicates were used and data were averaged. (c) Mass of oil/plant was calculated from total seed weight in CaMV35S:AGG3 and Glycinin:AGG3 overexpression lines compare to EV lines. Data presented are mean value of 6 plants of each line and error bars represent standard error (±SE). Significant difference at *P<0.05 and ** P<0.005, respectively (Student's t-test).

The percentage of oil on seed mass basis remained essentially unchanged in the transgenic seeds, suggesting no difference in the carbon partitioning due to the overexpression of AGG3 (FIG. 3A). Similarly, no significant differences were observed in the overall oil composition (Table 4). However, the higher total seed mass and seed number per plant resulted in significantly increased overall oil yield on a per plant basis. The oil content of EV lines was ~2.9 mg per 10 seeds, which increased to ~3.3-4 mg per 10 seeds in transgenic lines (FIG. 3B). Moreover, since the transgenic lines also produced more seeds per plant, a net increase of up to 20-35% and 25-55% in oil content per plant was observed in CaMV35S:AGG3 and Glycinin:AGG3 lines, respectively, compared to their corresponding EV controls (FIG. 3C).

Taken together, these data show that overexpression of AGG3 has a substantial effect on seed-related traits, including seed yield and overall oil production.

As already noted above, Clauss et al. (2011) and Shen et al. (2006) demonstrated that there is not necessarily a linear relationship between seed size and oil to protein to carbohydrate ratio: increased seed size, or mass, does not inevitably result in proportionately increased oil production and/or accumulation. Thus, as there is no direct correlation between increased seed size or mass and increased oil accumulation, the present results evidence a surprising benefit from expressing AGG3 in *Camelina*, i.e., concomitant proportionate oil production/accumulation accompanying higher total seed mass and seed number per plant. Therefore, on a per plant basis, AGG3-expressing transgenic *Camelina* plants produce an enhanced amount of oil compared to the amount of oil produced by an otherwise identical control plant grown under the same conditions.

TABLE 4

Fatty acid composition of Camelina seed oils in different CaMV35S:AGG3 and Glycinin:AGG3 overexpression and empty vector (EV) lines. Data represent mean values of 6 individual plants.

| Fatty Acid | 16:00 | 18:00 | 18:01 | 18:02 | 18:03 | 20:00 | 20:01 | 20:02 | 20:03 | 22:00 | 22:01 |
|---|---|---|---|---|---|---|---|---|---|---|---|
| CaMV35S:AGG3 | | | | | | | | | | | |
| EV | 7.63 | 2.88 | 11.49 | 23.19 | 33.03 | 2.06 | 12.76 | 2.22 | 1.23 | 0.39 | 3.07 |
| L1 | 7.58 | 2.95 | 11.84 | 23.34 | 32.33 | 2.15 | 12.87 | 2.19 | 1.18 | 0.41 | 3.11 |
| L2 | 7.06 | 2.78 | 10.12 | 20.16 | 37.19 | 2.40 | 12.64 | 2.21 | 1.47 | 0.4 | 3.45 |
| L3 | 7.35 | 2.67 | 10.73 | 22.66 | 36.18 | 2.09 | 11.64 | 2.17 | 1.23 | 0.39 | 2.83 |
| Glycinin:AGG3 | | | | | | | | | | | |
| EV | 7.14 | 2.59 | 11.09 | 21.57 | 34.32 | 2.08 | 13.60 | 2.39 | 1.37 | 0.40 | 3.40 |
| L1 | 7.23 | 3.15 | 10.82 | 21.06 | 34.86 | 2.55 | 12.89 | 2.11 | 1.33 | 0.49 | 3.46 |
| L2 | 7.44 | 3.21 | 12.59 | 22.49 | 32.60 | 2.30 | 12.75 | 2.03 | 1.15 | 0.42 | 2.96 |
| L3 | 7.59 | 3.00 | 12.16 | 23.46 | 32.12 | 2.15 | 12.69 | 2.16 | 1.13 | 0.40 | 3.09 |

The seed-specific traits were similar in both CaMV35S: AGG3 and Glycinin:AGG3 seeds, suggesting that a seed-specific promoter can be used in plants where improved vegetative growth may not be desired or required. It should be noted that while there is a need to improve the quality of oil in *Camelina* to make it more usable for biofuel applications (Nguyen et al., 2013), the demonstration herein that manipulation of fundamental developmental and physiological processes via the use of the type III Gγ protein AGG3 can lead to higher oil yield is significant, and has similar implications for other oil-producing crops, including oilseed crops. Combining different approaches, geared towards improving the quality as well as the quantity of seed oil, is therefore likely to result in higher amounts of desirable oil types in oil seed plants.

Example 4

*Camelina* Plants Overexpressing AGG3 Exhibit Higher Rates of Net Photosynthesis To investigate the physiological basis of higher growth rates and higher yield in transgenic plants, we measured the rates of net photosynthesis in transgenic plants. The photosynthetic rate directly affects the accumulation of starch in vegetative tissues, which is ultimately responsible for higher biomass and/or oil content. Similarly, starch that accumulates in the sink tissue (leaves) contributes to the size of seeds through translocation of photosynthates, a prerequisite for increased seed weight and size.

Leaf photosynthetic rates were measured with a portable photosynthetic system, LI6400XT (Li-COR, Lincoln, Nebr.). The conditions in the leaf chamber were calibrated similar to those in the greenhouse where plants were growing: 500 µmol $m^{-2}$ $s^{-1}$ photosynthetic photo flux density, 400 µmol $mol^{-1}$ $CO_2$, 23° C., and 60% relative humidity. Measurements were conducted on the $4^{th}$, $5^{th}$ and $6^{th}$ open leaves from the apical bud. Data were recorded five times for each sample, and six biological replicates were used for each measurement.

Figure 4:
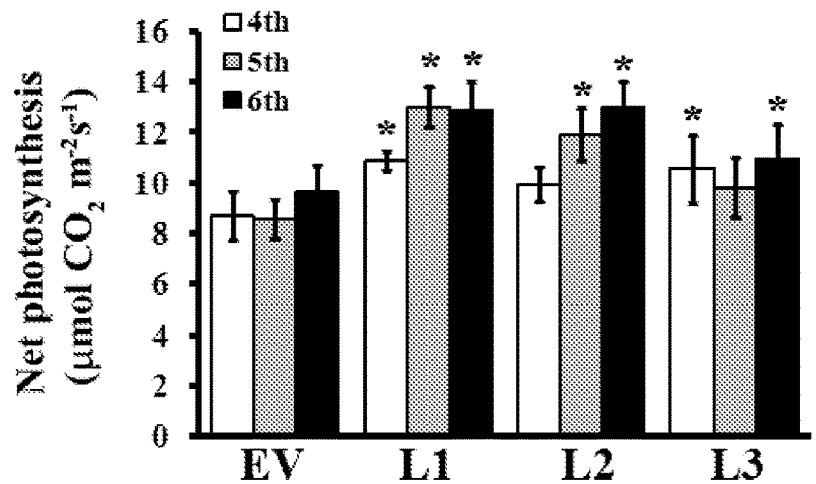
FIG. 4 shows measurement of the rate of photosynthesis of CaMV35S:AGG3 *Camelina* plants. Net photosynthesis, measured as the amount of $CO_2$ assimilated per second was determined on individual $4^{th}$, $5^{th}$ and $6^{th}$ leaves (from apical bud) of 4 weeks old empty vector (EV) and CaMV35S:AGG3 overexpression lines using a Li-COR 6400 gas exchange system. Six biological replicates of each line and five measurements for each leaf were used for data analysis. Error bars represent standard errors (±SE) and significant difference at *P<0.05 (Student's t-test).

The results shown in FIG. 4 demonstrate that the rate of photosynthesis of transgenic plants was significantly higher than that in EV control plants.

Example 5

Overexpression of AGG3 Results in Improved Stress Tolerance in Transgenic *Camelina* Plants The effect of abiotic stresses on plants overexpressing AGG3 has not been evaluated. Similarly, whether rice GS3 or DEP1 mutants have differential sensitivities to abiotic stresses is not known. GS3 and DEP1 encode for possible homologs of type III Gγ proteins (Fan et al., 2009; Huang et al., 2009; Takano-Kai et al., 2009; Mao et al., 2010).

Since stress responses of plants are a critical determinant of yield, we investigated whether overexpression of AGG3 in *Camelina* resulted in altered responsiveness to different stresses.

Effect of AGG3 on Response to Osmotic Stress

We first investigated the effect of AGG3 expression on response to osmotic stress.

Seeds from EV and CaMV:AGG3 transgenic plant lines produced as described in Example 2 were germinated on 0.5× Murashige & Skoog medium in the presence of either 1% sucrose (control) or 0.4M sucrose. Primary root length was measured from transgenic lines after 4 days of vertical growth. Seeds from EV and CaMV:AGG3 lines were also germinated on 0.5× Murashige & Skoog medium, 1% sucrose, and in the presence of 100 mM NaCl, and primary root length was measured after 5 days.

Figure 5:
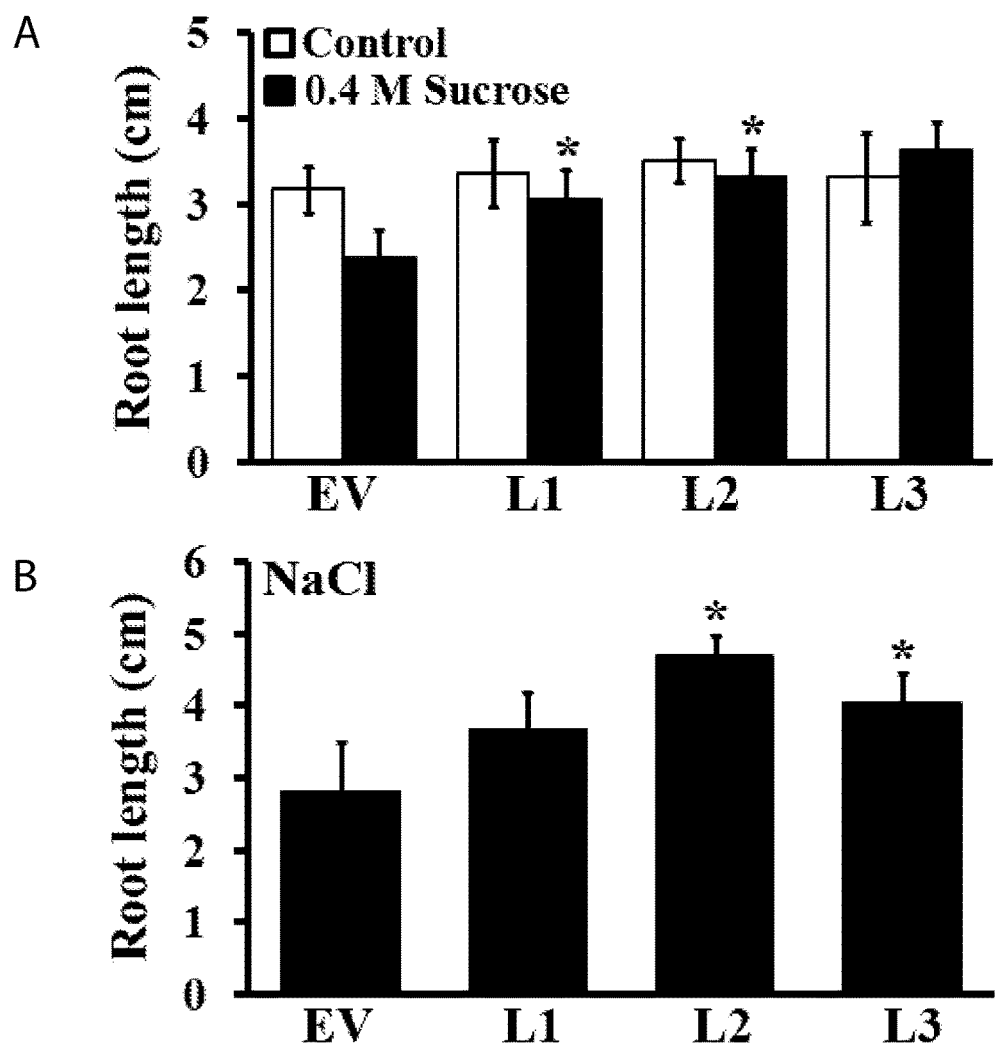
FIG. 5 shows high sucrose and NaCl hyposensitivity of CaMV:AGG3 plants. (a) Seeds from EV and CaMV:AGG3 lines were germinated on 0.5×MS in presence of either 1% sucrose (control) or 0.4M sucrose. Primary root length was measured from transgenic lines after 4 days of vertical growth. (b) Seeds from EV and CaMV:AGG3 lines were germinated on 0.5×MS, 1% sucrose and in presence of 100 mM NaCl and primary root length was measured after 5 days. All experiments were repeated three times and data were averaged, n=30 per line for each experiment. Error bars represent standard errors (±SE) and significant difference at *P<0.05 (Student's t-test).

The root growth of CaMV35S:AGG3 was less sensitive to osmotic stress induced due to the presence of 0.4 M Sucrose (FIG. 5a). In addition, CaMV35S:AGG3 transgenic seedlings showed hyposensitivity to salt stress in the presence of 100 mM NaCl (FIG. 5b), suggesting a general improvement of stress tolerance in the CaMV35S:AGG3 plants.

Effect of AGG3 on Response to Drought

We next explored the role of AGG3 in providing drought tolerance in overexpression lines.

Transgenic and control *Camelina* plants were grown in the green house (16 h light, 8 h dark, 23° C.) in a block arrangement. Each block contained 2 EV control plants and 2 plants from three different transgenic lines. Six independent blocks were used for each experiment. The position of plants was varied in each block. Ten-day old, well-watered plants were used for drought experiments. The plants were grown without water for additional 10 days, followed by re-watering for 7 days. Drought tolerance was determined by quantifying the number of surviving plants/total number of plants. Five independent biological replicates were performed, and data were averaged.

Since *Camelina* is inherently relatively drought tolerant, a large effect of low water-stress was not obvious. However, when 10 day-old plants were grown without water for an additional 10 days followed by re-watering, and drought recovery was estimated by evaluating the number of surviving plants after 7 days, differences were observed between the EV control and overexpression lines.

Figure 6:
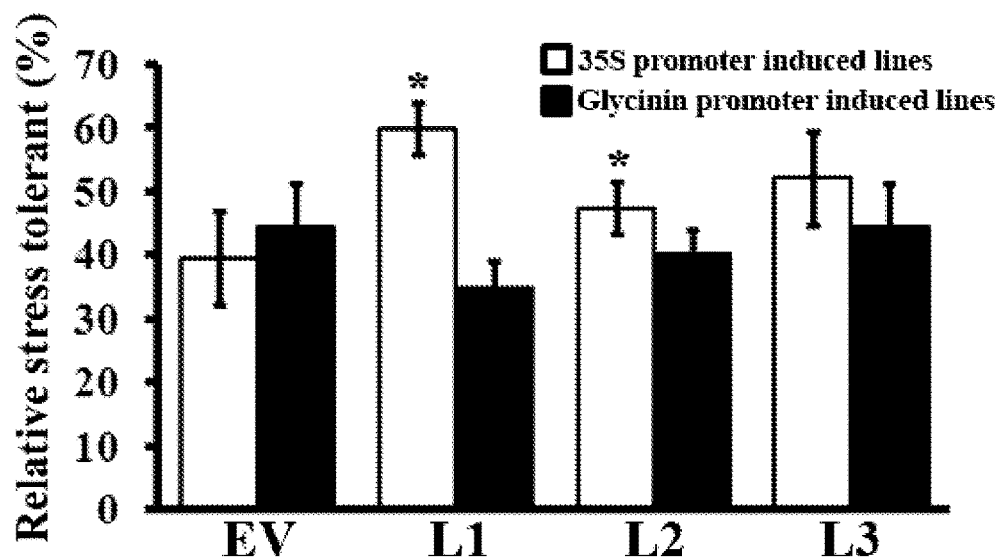
FIG. 6 shows drought response in transgenic *Camelina* plants. Watering of 10 day old plants was stopped for the next 10 days and then rewatered for 7 days. Number of survived plants/total plants was counted in 5 independent experiments. Error bars for all experiments represent standard errors (±SE) and significant difference at *P<0.05 (Student's t-test).

In five independent experiments, less than 40% of EV control plants survived this drought/recovery regime, whereas the survival of different CaMV35S:AGG3 lines varied from 50-60% (FIG. 6). The Glycinin:AGG3 transgenic lines showed no difference in survival from the EV control lines, as expected (FIG. 6).

Taken together, these results suggest a clear, positive role for AGG3 overexpression on multiple growth and development pathways that can lead to a significant increase in plant health and productivity.

Example 6

Overexpression of AGG3 Results in Better Redox Stress Tolerance in Transgenic *Camelina* Plants This example was designed to investigate the effect of AGG3 overexpression on redox stresses in plants. The results obtained demonstrate that transgenic *Camelina* lines that overexpress AGG3 are less sensitive to redox damage caused by the reducing agents reduced glutathione (GSH) or dithiotritol (DTT).

Seeds from EV and CaMV:AGG3 lines were germinated on 0.5× Murashige & Skoog medium in the presence of 1% sucrose (control), 2 mM dithiothreitol (DTT), or reduced glutathione (GSH). Seedling length was measured from transgenic lines after 2 days of vertical growth in etiolated conditions.

The extremely cysteine-rich region of type III Gγ proteins may be involved in the regulation of plant oxidative stress responses caused by changes in cellular redox homeostasis. The C-terminal region of AGG3 and its homologs contains 30-35% cysteine, which suggests their possible involvement in regulation of overall redox status.

Figure 7:
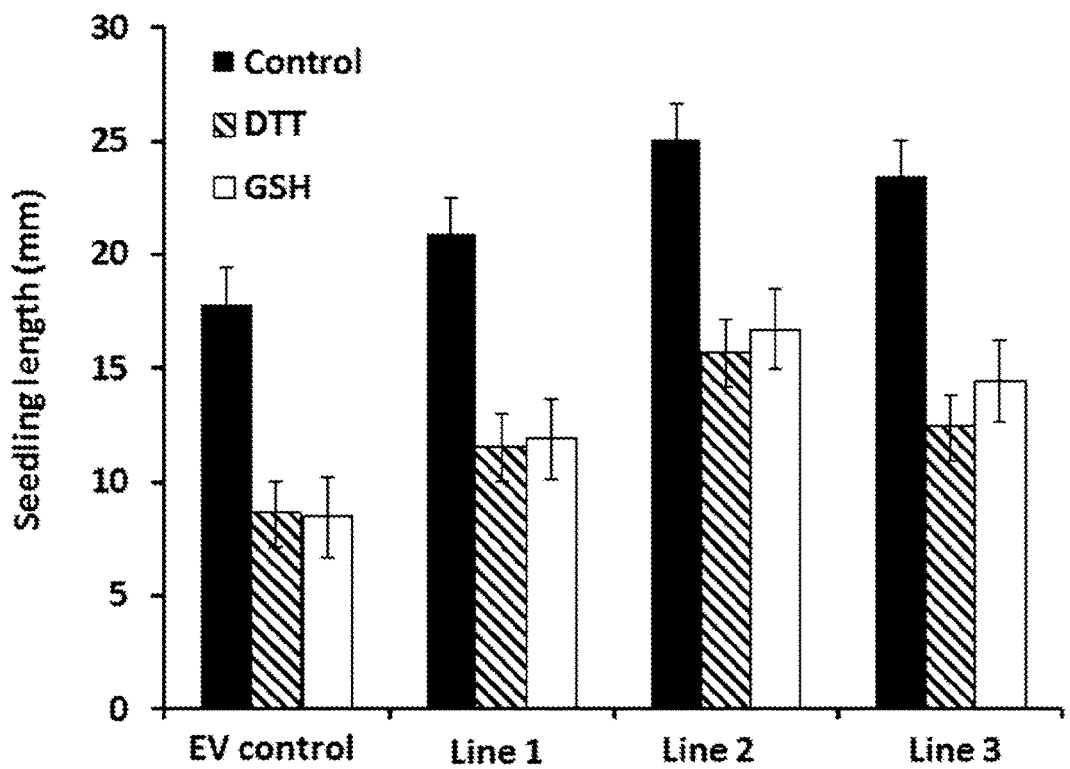
FIG. 7 shows response of group III Gγ overexpressing *Camelina* lines to oxidative stress induced by DTT and GSH. Seedlings of CaMV35S:AGG3 lines are less sensitive to oxidative damage caused by reduced glutathione (2 mM) or DTT (2 mM).

The transgenic plants continue to grow in the presence of dithiotritol (DTT) and reduced glutathione (GSH) at concentrations where non-transformed or only vector transformed plants cease growth (FIG. 7). After 2 days of growth on DTT or GSH containing media, 50-55% reduction in seedling length was observed for EV containing plants compared to plants growing on control media. In contrast the seedling length of transgenic line was reduced only by 35-45% under identical growth conditions. Thus, AGG3 expression resulted in a 10-15% enhancement in resistance to the effects of these reducing agents.

The addition of reducing agents, such as DTT or GSH, perturbs the homeostatic redox state of plants. The results shown in this example, suggest that transgenic Camelina plants overexpressing AGG3 have an increased tolerance to alterations in redox stateenvironment of plants. Disruptions of redox state can occur through the application of oxidizing or reducing agents (as shown in the present example) or though abiotic stresses such as cold, drought, flood, heat, ionizing and non-ionizing radiation, UV stress, ozone increases, increased sulfur dioxide, acid rain, air/water/soil pollutants, salt stress, heavy metals, mineralized soils, pesticides, or herbicides. Therefore, these results suggests that the transgenic plants would display better tolerance to additional abiotic stresses such as high salt concentration, high osmotic stress or high ozone. Together, this indicates that this technology can be used to produce plants which have overall higher growth and productivity in non-optimum environments.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

LITERATURE CITED

Bisht, N.C., Jez, J. M. and Pandey, S. (2011) An elaborate heterotrimeric G-protein family from soybean expands the diversity of plant G-protein networks. *New Phytologist* 190, 35-48.

Botella, J. R. (2012) Can heterotrimeric G proteins help to feed the world? *Trends in plant science* 17, 563-568.

Cabrera-Vera, T. M., Vanhauwe, J., Thomas, T. O., Medkova, M., Preininger, A., Mazzoni, M. R. and Hamm, H. E. (2003) Insights into G protein structure, function, and regulation. *Endocr Rev* 24, 765-781.

Carmo-Silva, A. E. and Salvucci, M. E. (2012) The temperature response of $CO_2$ assimilation, photochemical activities and Rubisco activation in *Camelina sativa*, a potential bioenergy crop with limited capacity for acclimation to heat stress. *Planta* 236, 1433-1445.

Chakravorty, D., Trusov, Y., Zhang, W., Acharya, B. R., Sheahan, M. B., McCurdy, D. W., Assmann, S. M. and Botella, J. R. (2011) An atypical heterotrimeric G-protein g-subunit is involved in guard cell $K^+$-channel regulation and morphological development in *Arabidopsis thaliana*. *Plant J* 67, 840-851.

Clauss, K., von Roepenack-Lahave, E., Bottcher, C., Roth, M. R., Welti, R., Erban, A., Kopka, J., Scheel, D., Milkowski, C., Strack, D. (2011) Overexpression of sinapine esterase BnSCE3 in oilseed rape seeds triggers global changes in seed metabolism. *Plant Physiology* 155 (3): 1127-1145.

Doyle, J. J., Schuler, M. A., Godette, W. D., Zenger, V., Beachy, R. N., Slightom, J. L. (1986) The glycosylated seed storage proteins of *Glycine max* and *Phaseolus vulgaris*. Structural homologies of genes and proteins. *Journal of Biological Chemistry* 261 (20), 9228-9238.

Fan, C., Yu, S., Wang, C. and Xing, Y. (2009) A causal C-A mutation in the second exon of GS3 highly associated with rice grain length and validated as a functional marker. *TAG. Theoretical and applied genetics. Theoretische and angewandte Genetik* 118, 465-472.

Fan, L. M., Zhang, W., Chen, J. G., Taylor, J. P., Jones, A. M. and Assmann, S. M. (2008) Abscisic acid regulation of guard-cell K+ and anion channels in Gb- and RGS-deficient *Arabidopsis* lines. *Proceedings of the National Academy of Sciences of the United States of America* 105, 8476-8481.

Ghamkhar, K., Croser, J., Aryamanesh, N., Campbell, M., Kon'kova, N. and Francis, C. (2010) Camelina (*Camelina sativa* (L.) Crantz) as an alternative oilseed: molecular and ecogeographic analyses. *Genome/National Research Council Canada=Genome/Conseil national de recherches Canada* 53, 558-567.

Huang, X., Qian, Q., Liu, Z., Sun, H., He, S., Luo, D., Xia, G., Chu, C., Li, J. and Fu, X. (2009) Natural variation at the DEP1 locus enhances grain yield in rice. *Nature genetics* 41, 494-497.

Jammes, F., Song, C., Shin, D., Munemasa, S., Takeda, K., Gu, D., Cho, D., Lee, S., Giordo, R., Sritubtim, S., Leonhardt, N., Ellis, B. E., Murata, Y. and Kwak, J. M. (2009) MAP kinases MPK9 and MPK12 are preferentially expressed in guard cells and positively regulate ROS-mediated ABA signaling. *Proceedings of the National Academy of Sciences of the United States of America* 106, 20520-20525.

Kim, H. S., Oh, J. M., Luan, S., Carlson, J. E. and Ahn, S. J. (2013) Cold stress causes rapid but differential changes in properties of plasma membrane $H^+$-ATPase of camelina and rapeseed. *Journal of plant physiology*.

Lam, E., Chua N. H. (1990) GT-1 binding site confers light responsive expression in transgenic tobacco. *Science* 248 (2954), 471-474.

Li, S., Liu, Y., Zheng, L., Chen, L., Li, N., Corke, F., Lu, Y., Fu, X., Zhu, Z., Bevan, M. W. and Li, Y. (2012) The plant-specific G protein g subunit AGG3 influences organ size and shape in *Arabidopsis thaliana*. *The New phytologist* 194, 690-703.

Liang, C., Liu, X., Yiu, S. M. and Lim, B. L. (2013) De novo assembly and characterization of *Camelina sativa* transcriptome by paired-end sequencing. *BMC genomics* 14, 146.

Lu, C. and Kang, J. (2008) Generation of transgenic plants of a potential oilseed crop *Camelina sativa* by *Agrobacterium*-mediated transformation. *Plant cell reports* 27, 273-278.

Lu, S., Bahn, S. C., Qu, G., Qin, H., Hong, Y., Xu, Q., Zhou, Y. and Wang, X. (2013) Increased expression of phospholipase Da1 in guard cells decreases water loss with improved seed production under drought in *Brassica napus*. *Plant biotechnology journal* 11, 380-389.

Mao, H., Sun, S., Yao, J., Wang, C., Yu, S., Xu, C., Li, X. and Zhang, Q. (2010) Linking differential domain functions of the GS3 protein to natural variation of grain size in rice. *Proceedings of the National Academy of Sciences of the United States of America* 107, 19579-19584.

Nakashima, K. and Yamaguchi-Shinozaki, K. (2013) ABA signaling in stress-response and seed development. *Plant cell reports*.

Nguyen, H. T., Silva, J. E., Podicheti, R., Macrander, J., Yang, W., Nazarenus, T. J., Nam, J. W., Jaworski, J. G., Lu, C., Scheffler, B. E., Mockaitis, K. and Cahoon, E. B. (2013) *Camelina* seed transcriptome: a tool for meal and oil improvement and translational research. *Plant biotechnology journal*.

Offermanns, S. (2003) G-proteins as transducers in transmembrane signalling. *Prog Biophys Mol Biol* 83, 101-130.

Oh, J. E., Kwon, Y., Kim, J. H., Noh, H., Hong, S. W. and Lee, H. (2011) A dual role for MYB60 in stomatal regulation and root growth of *Arabidopsis thaliana* under drought stress. *Plant molecular biology* 77, 91-103.

Pandey, S., Chen, J. G., Jones, A. M. and Assmann, S. M. (2006) G-protein complex mutants are hypersensitive to abscisic acid regulation of germination and postgermination development. *Plant physiology* 141, 243-256.

Parry, M. A. and Hawkesford, M. J. (2010) Food security: increasing yield and improving resource use efficiency. *The Proceedings of the Nutrition Society* 69, 592-600.

Parry, M. A. and Hawkesford, M. J. (2012) An integrated approach to crop genetic improvement. *Journal of integrative plant biology* 54, 250-259.

Peskan-Berghofer, T., Neuwirth, J., Kusnetsov, V. and Oelmuller, R. (2005) Suppression of heterotrimeric G-protein b-subunit affects anther shape, pollen development and inflorescence architecture in tobacco. *Planta* 220, 737-746.

Peterhansel, C. and Offermann, S. (2012) Re-engineering of carbon fixation in plants—challenges for plant biotechnology to improve yields in a high-$CO_2$ world. *Current opinion in biotechnology* 23, 204-208.

Potters, G., Horemans, N. and Jansen, M. A. K. (2010) The cellular redox state in plant stress biology—A charging concept. *Plant Physiology and Biochemistry* 48(5), 292-300.

Qin, F., Shinozaki, K. and Yamaguchi-Shinozaki, K. (2011) Achievements and challenges in understanding plant abiotic stress responses and tolerance. *Plant & cell physiology* 52, 1569-1582.

Rojas, C. A., Hemerly, A. S. and Ferreira, P. C. (2010) Genetically modified crops for biomass increase. Genes and strategies. *GM crops* 1, 137-142.

Roy Choudhury, S., Bisht, N.C., Thompson, R., Todorov, O. and Pandey, S. (2011) Conventional and novel Gg protein families constitute the heterotrimeric G-protein signaling network in soybean. *PloS one* 6, e23361.

Roy Choudhury, S. and Pandey, S. (2013) Specific subunits of heterotrimeric G-proteins play important roles during nodulation in soybean. *Plant physiology*.

Ruan, Y. L., Patrick, J. W., Bouzayen, M., Osorio, S. and Fernie, A. R. (2012) Molecular regulation of seed and fruit set. *Trends in plant science* 17, 656-665.

Temple, B. R. and Jones, A. M. (2007) The plant heterotrimeric G-protein complex. *Annual review of plant biology* 58, 249-266.

Thung, L., Trusov, Y., Chakravorty, D. and Botella, J. R. (2012) Gg1+Gg2+Gg3=Gb: the search for heterotrimeric G-protein g subunits in *Arabidopsis* is over. *Journal of plant physiology* 169, 542-545.

Trusov, Y., Chakravorty, D. and Botella, J. R. (2012) Diversity of heterotrimeric G-protein g subunits in plants. *BMC research notes* 5, 608.

Trusov, Y., Zhang, W., Assmann, S. M. and Botella, J. R. (2008) Gg1+Gg2 not equal to Gb: heterotrimeric G protein Gg-deficient mutants do not recapitulate all phenotypes of Gb-deficient mutants. *Plant physiology* 147, 636-649.

Shen, B., Sinkevicius K. W., Selinger D. A., Tarczynski M. C. (2006) The homeobox gene GLABRA2 affects seed oil content in *Arabidopsis*. *Plant Molecular Biology* 60 (3): 377-387.

Ueguchi-Tanaka, M., Fujisawa, Y., Kobayashi, M., Ashikari, M., Iwasaki, Y., Kitano, H. and Matsuoka, M. (2000) Rice dwarf mutant d1, which is defective in the a subunit of the heterotrimeric G protein, affects gibberellin signal transduction. *Proceedings of the National Academy of Sciences of the United States of America* 97, 11638-11643.

Urano, D., Chen, J. G., Botella, J. R. and Jones, A. M. (2013) Heterotrimeric G protein signalling in the plant kingdom. *Open biology* 3, 120186.

Utsunomiya, Y., Samejima, C., Takayanagi, Y., Izawa, Y., Yoshida, T., Sawada, Y., Fujisawa, Y., Kato, H. and Iwasaki, Y. (2011) Suppression of the rice heterotrimeric G protein b-subunit gene, RGB1, causes dwarfism and browning of internodes and lamina joint regions. *Plant J* 67, 907-916.

Wang, X. Q., Ullah, H., Jones, A. M. and Assmann, S. M. (2001) G protein regulation of ion channels and abscisic acid signaling in *Arabidopsis* guard cells. *Science* (New York, N.Y 292, 2070-2072.

Wang, Y., Beaith, M., Chalifoux, M., Ying, J., Uchacz, T., Sarvas, C., Griffiths, R., Kuzma, M., Wan, J. and Huang, Y. (2009) Shoot-specific down-regulation of protein farnesyltransferase (a-subunit) for yield protection against drought in canola. *Molecular plant* 2, 191-200.

Wang, Y., Ying, J., Kuzma, M., Chalifoux, M., Sample, A., McArthur, C., Uchacz, T., Sarvas, C., Wan, J., Dennis, D. T., McCourt, P. and Huang, Y. (2005) Molecular tailoring of farnesylation for plant drought tolerance and yield protection. *Plant J* 43, 413-424.

Zhang, Y., Yu, L., Yung, K. F., Leung, D. Y., Sun, F. and Lim, B. L. (2012) Over-expression of AtPAP2 in *Camelina sativa* leads to faster plant growth and higher seed yield. *Biotechnology for biofuels* 5, 19.

Amino Acid and Nucleotide Sequences

```
Full length AGG3 cDNA Coding Sequence, At5g20635
                                                 (SEQ ID NO: 1)
ATGTCTGCTCCTTCTGGCGGTGGCGAAGGAGGAGGAAAAGAATCAGCTGCTGGTGGAGTGAG

TTCATCGTCTCTTGCTCCGTCGTCTCTACCACCGCCTCGTCCTAAGTCTCCACCAGAGTATC

CAGATTTGTACGGGAAACGCAGAGAGGCGGCGAGAGTTCAGATGCTCGAGAGAGAGATTGGT

TTTCTCGAGGGCGAAATTAAATTCATCGAAGGCGTACAACCGGCATCTAGATGCATCAAAGA

AGTCTCTGATTTTGTTGTTGCAAATTCTGACCCATTGATCCCTGCACAACGAAAAAGTCGAA

GATCCTTCCGGTTCTGGAAGTGGCTCTGTGGCCCATGTTTGAGCCTGGTGAGTTTCTGCTGT

TGCTGCCAATCCAAATGTTCGTGCCATCTGAGGAAACCCAAGTGCTGCAACTGTACATCTTG
```

-continued

CAGCTGTATAGGGTCCAAATGCTGTGACGGGTCATGCTGCTCAAACATTTGTTGTTGCCCGA

GACTAAGCTGCCCGAGCTGTTCATGCTTCCGAGGTTGCTGGTGTTCTTGTCCGGACATGTCT

TGCTGCATTCCCAGCTGTTTCCGCAGTTGCAGTTGCACTCGACCGTCGTGTCTGAATAAAAA

GAAGAGCTCATGCTGCAGCTGCAACTGCAAGATCAGATGGTCATCTTGTTTTAGTTGTCCCA

AGGTACGACTTTGTTCTTGTTGTTTTTGCAATTGTAAAAATCTATGTTCTAATCCTTGTTGT

TTAGCTTTCTAA

Full length AGG3 Genomic Sequence, At5g20635

(SEQ ID NO: 2)
ACTACTACACACTCATCTCTCTCTTTCTCTTTTTCTTTCTTCTTTGCATTGTTTTTCTCA

CTCACTCGCCGCTTCCTCTTCTCTTCTTCTGGTTCACTTCTCTCCTAAGTAATAACACCACT

GCATGTTTCTCTCTTGAGACACTCCAAACCATTTCTCTCCGAAAATGTCTGCTCCTTCTGGC

GGTGGCGAAGGAGGAGGAAAAGAATCAGCTGCTGGTGGAGTGAGTTCATCGTCTCTTGCTCC

GTCGTCTCTACCACCGCCTCGTCCTAAGTCTCCACCAGAGTATCCAGATTTGTACGGGAAAC

GCAGAGAGGCGGCGAGAGTTCAGATGCTCGAGAGAGAGATTGGTTTTCTCGAGGCAAGTCTC

TCTCTCTCAATACTTTTATTTTATTACTACTACTACTACTATTTTAAAAACAGTCCTTTTCA

TTCTTATTTTATTCATAAAATCTGTGCCATTTTTGATTACTCTGAGGAAGTGTCCCAATATT

TTGAATTTCATCACTCCTTTGTTTTTATTATTATTACTCTCTCTTTTTCAAAAAAAATTGGT

ACTAGTATTAGTTTCTGATTAGTAAATTAATTAATGCTAATTAACCTCTCTTGTATAACTAA

ATAATCCAGTTGTAGTACTATTTGATTTTTGGTTGTTGTGAGAAAAGAGTGTTAAAACTTGG

TCCCTACTATATCCAGGTTGGTTTGGACTCTGGACCGTTGTGTTATGTTTTGACAGCAATTA

TAGAAACCCAAGACATTTAATTTATATTTGTTCTCTTTGATGCTCCCAAAAAGAATTATTAA

TTTCTGTCATCAGACACATTTCTCTATTTCTATATCTAATTAAATTCAAACTAGTACTATGA

TATGCCAACAAGGGCTTTAACCACTTAAACTAATGCATGTTTTCTTAATTGAAAATTAATTT

GAATCATTTCTCTTAGTAATTTTTTTGTTAGTTGAGGGAGTTTCAACGGATCTATTCTTTAA

AAACTAAATTAATTGGGTTCCTATGCTTTTCGTTAATCAGGATTTTTTTGGGTTATAGAAT

ATTGTTAGTAGTTACATTCTGTTTTAAAATTAAGGATACATAAAAAAAAAAAAGTAAAAAAA

ATGTTAAAGGTAAAAAAAAAAAATGTGATCATGTTGTAGTGTGAAGTGACCGATGAGACGCC

CATTTACTCAGTTGTTTGCATCACTGAGGCCTAATGTGTTCGTGCATGTGTACTATGAAAGT

GAGTGCTTAGTCAAAGAGAGTATTAAAGGGAAAAATACATAAAGATAAAGAAGAAAAGCATT

AGAAGCAAAGTAGGGAAAGATCTAAAAAATATATTGAATTTGGTTAGCTTCCATTGCTGATT

TTGTTTTGTTTTGCTTTGCCATATCAATCAATTTTTGTGAAAGCTTTTGTCTTTATTGCTAT

CTGCGTTTGAAAGGACCAATTCTTGGTCACCTTTTTCCTCATGTTGCTTTCTCATTTCCCCC

TCTATGATTACTTTTTCTATAGTGCATATAATTGGTTGTAATTAAATTATTTTTTACACTGT

ATATGTTTAGTTTAATATGCAATTCTTGTTTTGTCCCATTAGTGTCTACTTAATTTAGATCT

TCTCTTTTTTTAACCAAGCAAATACAATTTGGTTGATTAATGAAATGATGTTTCTTAACCAA

TATTTCGAATGTCGTTATGATCAGGGCGAAATTAAATTCATCGAAGGCGTACAACCGGCATC

TAGATGCATCAAAGAGTGAGTGTTTTAAAAACATTCTATCAGTTTTTATCAGTTTGGTTTAT

TGATAAAAGAAATATTTTGTTGTGGCAGAGTCTCTGATTTTGTTGTTGCAAATTCTGACCCA

TTGATCCCTGCGTAAGCGTATTTCTAGTTCACTCAATGACTTCACACTTTTCTCGTACTTTG

CCCGCTCTTACAATTCCGTTGTGCTGTTTTTGTCTTCTCATATAAATAGACAACGAAAAAGT

CGAAGATCCTTCCGGTTCTGGAAGTGGCTCTGGTAAGCATTTAAATTGGAACATTATATTTT

GAAAATATTTTATTTTCGCAATTTTATATAAAATTTGCATAAGACCTCAACTAGTAAGAAAT

-continued

GTTTTTAGCCAATGCTTTTAATCTTAGATTTTGCTAGAATTACTGATATGTGTAGCTATCTG

AATAAAGTGATACTAATTAATTAACTCAATGCAGTGGCCCATGTTTGAGCCTGGTGAGTTTC

TGCTGTTGCTGCCAATCCAAATGTTCGTGCCATCTGAGGAAACCCAAGTGCTGCAACTGTAC

ATCTTGCAGCTGTATAGGGTCCAAATGCTGTGACGGGTCATGCTGCTCAAACATTTGTTGTT

GCCCGAGACTAAGCTGCCCGAGCTGTTCATGCTTCCGAGGTTGCTGGTGTTCTTGTCCGGAC

ATGTCTTGCTGCATTCCCAGCTGTTTCCGCAGTTGCAGTTGCACTCGACCGTCGTGTCTGAA

TAAAAAGAAGAGCTCATGCTGCAGCTGCAACTGCAAGATCAGATGGTCATCTTGTTTTAGTT

GTCCCAAGGTACGACTTTGTTCTTGTTGTTTTTGCAATTGTAAAAATCTATGTTCTAATCCT

TGTTGTTTAGCTTTCTAATTAAACTTTATTATTATTATAATCATTATAGCTGTTTCCTCTAT

TTTTTGTTCAAATTTTTTCTTAATCTCTTAAAGGAAGCAACACTTTCTTGATTTTGT

Full length AGG3 Protein Sequence, At5g20635
(SEQ ID NO: 3)
MSAPSGGGEGGGKESAAGGVSSSSLAPSSLPPPRPKSPPEYPDLYGKRREAARVQMLEREIG

FLEGEIKFIEGVQPASRCIKEVSDFVVANSDPLIPAQRKSRRSFRFWKWLCGPCLSLVSFCC

CCQSKCSCHLRKPKCCNCTSCSCIGSKCCDGSCCSNICCCPRLSCPSCSCFRGCWCSCPDMS

CCIPSCFRSCSCTRPSCLNKKKSSCCSCNCKIRWSSCFSCPKVRLCSCCFCNCKNLCSNPCC

LAF

---

What is claimed:

1. A transgenic plant, other than a rice plant or *Arabidopsis*, wherein said transgenic plant comprises within its genome a heterologous nucleotide sequence that encodes a type III Gγ protein, wherein said heterologous nucleotide sequence comprises the nucleotide sequence set forth in SEQ ID NO:1 that encodes the type III Gγ protein comprising the amino acid sequence set forth in SEQ ID NO:3, and wherein said transgenic plant expressing said type III Gγ protein comprising the amino acid sequence set forth in SEQ ID NO:3 exhibits enhanced resistance to an abiotic stress that disrupts the normal redox state of plants compared to the resistance to said abiotic stress exhibited by a control plant of the same species lacking said heterologous nucleotide sequence comprising the nucleotide sequence set forth in SEQ ID NO:1 that encodes said type III Gγ protein comprising the amino acid sequence set forth in SEQ ID NO:3 and grown under the same conditions.

2. The transgenic plant of claim 1, wherein said heterologous nucleotide sequence comprising the nucleotide sequence set forth in SEQ ID NO:1 that encodes said type III Gγ protein comprising the amino acid sequence set forth in SEQ ID NO:3, is expressed under the control of a constitutive or tissue-specific promoter.

3. The transgenic plant of claim 1, wherein said abiotic stress that disrupts the normal redox state of plants is selected from the group consisting of cold, heat, drought, flood, ionizing radiation, non-ionizing radiation, acid rain, an air pollutant, a water pollutant, a soil pollutant, mineralized soil, a pesticide, and a herbicide.

4. The transgenic plant of claim 3, wherein said air pollutant is selected from the group consisting of elevated carbon dioxide, ozone, and sulfur dioxide; and wherein said water or soil pollutant is selected from the group consisting of a salt and a heavy metal.

5. The transgenic plant of claim 1, wherein said enhanced resistance to said abiotic stress that disrupts the normal redox state of plants is in the range from about 10% to about 15% greater than that exhibited by said control plant of the same species lacking said heterologous nucleotide sequence and when both plants are grown under the same conditions.

6. The transgenic plant of claim 1, wherein expression of said heterologous nucleotide sequence comprising the nucleotide sequence set forth in SEQ ID NO:1 that encodes said type III Gγ protein comprising the amino acid sequence set forth in SEQ ID NO:3 in cells of said plant results in production of an enhanced amount of oil in seeds thereof compared to the amount of oil produced in seeds by said control plant of the same species lacking said heterologous nucleotide sequence comprising the nucleotide sequence set forth in SEQ ID NO:1 that encodes said type III Gγ protein comprising the amino acid sequence set forth in SEQ ID NO:3 and grown under the same conditions.

7. The transgenic plant of claim 1, wherein said transgenic plant is a food crop plant or an oil crop plant.

8. The transgenic plant of claim 7, wherein said food crop plant is selected from the group consisting of a cereal crop, a protein crop, a root, a tuber, a sugar crop, a fruit crop, a vegetable crop, a nut crop, a forage grass, a turf grass, a forage legume, a drug crop, a spice crop, and a flavoring crop.

9. A method of making a transgenic plant, other than a rice plant or *Arabidopsis*, which exhibits enhanced resistance to an abiotic stress that disrupts the normal redox state of plants, comprising expressing a heterologous nucleotide sequence that encodes a type III Gγ protein, wherein said heterologous nucleotide sequence comprises the nucleotide sequence set forth in SEQ ID NO:1 that encodes the type III Gγ protein comprising the amino acid sequence set forth in SEQ ID NO:3, within cells of said transgenic plant,
wherein expression of said heterologous nucleotide sequence comprising the nucleotide sequence set forth in SEQ ID NO:1 that encodes the type III Gγ protein comprising the amino acid sequence set forth in SEQ ID NO:3 enhances resistance to said abiotic stress that disrupts the normal redox state of plants in said transgenic plant compared to the resistance to said abiotic stress that disrupts the normal redox state of plants exhibited by a control plant of the same species lacking said heterologous nucleotide sequence comprising the nucleotide sequence set forth in SEQ ID NO:1 that encodes the type III Gγ protein comprising the amino acid sequence set forth in SEQ ID NO:3 and grown under the same conditions.

10. A method of making a transgenic oil crop plant that produces an enhanced amount of oil in seeds thereof, comprising:
expressing a heterologous nucleotide sequence comprising the nucleotide sequence set forth in SEQ ID NO:1 that encodes a type III Gγ protein comprising the amino acid sequence set forth in SEQ ID N0:3 in cells of said oil crop plant,
wherein expression of said heterologous nucleotide sequence comprising the nucleotide sequence set forth in SEQ ID NO:1 that encodes said type III Gγ protein comprising the amino acid sequence set forth in SEQ ID NO:3 is enhanced,
wherein the amount of oil produced in seeds by said transgenic oil crop plant is enhanced compared to the amount of oil produced in seeds by a control plant of the same species lacking said heterologous nucleotide sequence comprising the nucleotide sequence set forth in SEQ ID NO:1 that encodes a type III Gγ protein comprising the amino acid sequence set forth in SEQ ID N0:3 and grown under the same conditions.

11. The method of claim 10, wherein said oil crop plant is selected from the group consisting of corn, soybean, canola (rapeseed), wheat, peanut, palm, coconut, safflower, sesame, cottonseed, sunflower, flax, olive, safflower, sugarcane, castor bean, *Camelina*, switchgrass, *Miscanthus*, and *Jatropha*.

* * * * *